United States Patent
Okada et al.

(10) Patent No.: US 11,723,963 B2
(45) Date of Patent: *Aug. 15, 2023

(54) PEPTIDE ANALOGS CAPABLE OF ENHANCING STIMULATION OF A GLIOMA-SPECIFIC CTL RESPONSE

(71) Applicant: University of Pittsburgh—Of the Commonwealth System of Higher Education, Pittsburgh, PA (US)

(72) Inventors: Hideho Okada, Pittsburgh, PA (US); Walter J. Storkus, Glenshaw, PA (US)

(73) Assignee: UNIVERSITY OF PITTSBURGH—OF THE COMMONWEALTH SYSTEM OF HIGHER EDUCATION, Pittsburgh, PA (US)

(*) Notice: Subject to any disclaimer, the term of this patent is extended or adjusted under 35 U.S.C. 154(b) by 446 days.

This patent is subject to a terminal disclaimer.

(21) Appl. No.: 16/572,019

(22) Filed: Sep. 16, 2019

(65) Prior Publication Data

US 2020/0246442 A1 Aug. 6, 2020

Related U.S. Application Data

(63) Continuation of application No. 15/205,203, filed on Jul. 8, 2016, now Pat. No. 10,434,155, which is a continuation of application No. 14/951,821, filed on Nov. 25, 2015, now abandoned, which is a continuation of application No. 14/688,376, filed on Apr. 16, 2015, now abandoned, which is a continuation of application No. 14/478,458, filed on Sep. 5, 2014, now abandoned, which is a continuation of application No. 12/561,973, filed on Sep. 17, 2009, now Pat. No. 8,859,488, which is a continuation of application No. 11/231,618, filed on Sep. 21, 2005, now Pat. No. 7,612,162.

(60) Provisional application No. 60/611,797, filed on Sep. 21, 2004.

(51) Int. Cl.
*A61K 39/00* (2006.01)
*C07K 14/715* (2006.01)
*A61K 38/00* (2006.01)

(52) U.S. Cl.
CPC ...... *A61K 39/0011* (2013.01); *C07K 14/7155* (2013.01); *A61K 38/00* (2013.01); *A61K 2039/55516* (2013.01); *A61K 2039/572* (2013.01)

(58) Field of Classification Search
CPC .................................................. A61K 39/0011
See application file for complete search history.

(56) References Cited

U.S. PATENT DOCUMENTS

| | | | |
|---|---|---|---|
| 5,057,540 A | 10/1991 | Kensil et al. | |
| 6,162,432 A | 12/2000 | Wallner et al. | |
| 7,297,337 B2 | 11/2007 | Storkus et al. | |
| 7,338,929 B2 | 3/2008 | Debinski et al. | |
| 7,354,584 B2 | 4/2008 | Reed et al. | |
| 7,612,162 B2 | 11/2009 | Okada et al. | |
| 7,842,294 B2 | 11/2010 | Andersen et al. | |
| 7,902,143 B2 | 3/2011 | Okano | |
| 7,943,138 B2 | 5/2011 | Ciesielski et al. | |
| 8,007,810 B2 | 8/2011 | Fikes et al. | |
| 8,097,256 B2 | 1/2012 | Yu et al. | |
| 8,114,407 B2 | 2/2012 | Storkus et al. | |
| 8,574,584 B2 | 11/2013 | Storkus et al. | |
| 8,859,488 B2 | 10/2014 | Okada et al. | |
| 10,874,730 B2 | 12/2020 | Okada | |
| 2002/0168360 A1 | 11/2002 | Dingivan et al. | |
| 2002/0182219 A1 | 12/2002 | Debinski et al. | |
| 2005/0002934 A1 | 1/2005 | Reed | |
| 2005/0048550 A1 | 3/2005 | Storkus et al. | |
| 2005/0153923 A1 | 7/2005 | Kinch | |
| 2005/0281783 A1 | 12/2005 | Kinch et al. | |
| 2006/0034856 A1 | 2/2006 | Kosmatopoulos et al. | |
| 2006/0084609 A1 | 4/2006 | Scheinberg et al. | |
| 2006/0099652 A1 | 5/2006 | Gately et al. | |
| 2007/0167375 A1 | 7/2007 | Okada et al. | |
| 2008/0311141 A1 | 12/2008 | Yu et al. | |
| 2009/0041732 A1 | 2/2009 | Ciesielski et al. | |
| 2010/0008940 A1 | 1/2010 | Okada et al. | |
| 2011/0223187 A1 | 9/2011 | Shahabi et al. | |

(Continued)

FOREIGN PATENT DOCUMENTS

| | | | |
|---|---|---|---|
| EP | 1 835 027 A1 | 9/2007 | |
| EP | 2 172 211 A1 | 4/2010 | |
| EP | 2 228 072 A1 | 9/2010 | |

(Continued)

OTHER PUBLICATIONS

Bergmann et al. (J. Immunol. Oct. 15, 1996; 157 (8): 3242-9).*
Chang et al. (Proc. Natl. Acad. Sci. USA. Nov. 22, 2005; 102 (47): 17107-12).*
Urban et al. (Proc. Natl. Acad. Sci. USA. Feb. 15, 1994; 91 (4):1534-8).*
Chen et al. (Arthritis Rheumatol. Feb. 2014; 66 (2): 284-94).*

(Continued)

*Primary Examiner* — Stephen L Rawlings
(74) *Attorney, Agent, or Firm* — Leydig, Voit & Mayer, Ltd.

(57) ABSTRACT

The invention provides a peptide derived from the interleukin-13 receptor α2, which serves as a HLA-A2-restricted cytotoxic T lymphocyte (CTL) epitope. The invention can be used as a vaccine for glioma and can be formulated into compositions for medical or veterinary use. In addition, the invention provides the use of a peptide derived from the Eph family of tyrosine kinase receptors which can be also used as a vaccine for glioma and can be formulated into compositions for medical or veterinary use.

8 Claims, 9 Drawing Sheets

Specification includes a Sequence Listing.

(56) References Cited

U.S. PATENT DOCUMENTS

2012/0052080 A1    3/2012  Okada

FOREIGN PATENT DOCUMENTS

| | | |
|---|---|---|
| JP | 2004-353820 A | 12/2004 |
| JP | 2006-526628 A | 11/2006 |
| JP | 2009-511637 A | 3/2009 |
| JP | 2019-123745 A | 7/2019 |
| WO | WO 93/06866 A2 | 4/1993 |
| WO | WO 95/22317 A1 | 8/1995 |
| WO | WO 96/18409 A1 | 6/1996 |
| WO | WO 01/58479 A1 | 8/2001 |
| WO | WO 01/62979 A2 | 8/2001 |
| WO | WO 02/098370 A2 | 12/2002 |
| WO | WO 03/091383 A2 | 11/2003 |
| WO | WO 2005/012350 A2 | 2/2005 |
| WO | WO 2005/028505 A2 | 3/2005 |
| WO | WO 2005/067460 A2 | 7/2005 |
| WO | WO 2006/034334 A2 | 3/2006 |
| WO | WO 2006/062094 A1 | 6/2006 |
| WO | WO 2007/109812 A2 | 9/2007 |
| WO | WO 2007/109813 A1 | 9/2007 |
| WO | WO 2008/039969 A2 | 4/2008 |
| WO | WO 2010/037513 A1 | 4/2010 |
| WO | WO 2010/065876 A2 | 6/2010 |

OTHER PUBLICATIONS

Delamarre et al. (Science. Mar. 11, 2005; 307 (5715): 1630-4).*
Holmes (Expert Opinion on Investigational Drugs. 2001, 10: 511-519).*
Sugiyama, H., "WT1 (Wilms' Tumor Gene 1): Biology and Cancer Immunotherapy," *Jpn. J. Clin. Oncol.*, 40(5): 377-387 (2010).
Clinical Trial NCT00874861 (Apr. 3, 2009).
History of Changes for Study: NCT00345163 (Jun. 26, 2006).
History of Changes for Study: NCT00874861 (Apr. 2, 2009).
Okada et al., "Induction of CD8+ T-Cell Responses Against Novel Glioma-Associated Antigen Peptides and Clinical Activity by Vaccinations With α-Type 1 Polarized Dendritic Cells and Polyinosinic-Polycytidylic Acid Stabilized by Lysine and Carboxymethylcellulose in Patients With Recurrent Malignant Glioma," *J. Clin. Oncol.*, 29(3): 330-336 (2011).
Australian Patent Office, Patent Examination Report No. 1, dated Feb. 10, 2014, in Australian Patent Application No. 2100293522.
European Patent Office, Extended European Search Report in European Patent Application No. 18211075.9, 13 pp. (Apr. 8, 2019).
Japanese Patent Office, Decision of Refusal, in Japanese Patent Application No. 526099/2013 (dated Mar. 15, 2016).
Ahmed et al., "Nonenzymic Reactivation of Reduced Bovine Pancreatic Ribonuclease by Air Oxidation and by Glutathione," *The Journal of Biological Chemistry*, 250(21): 8477-8482 (Nov. 10, 1975).
Albericio et al., "Improved approach for anchoring $N^\alpha$-9-fluorenylmethyloxycarbonylamino acids as p-alkoxybenzyl esters in solid-phase peptide synthesis," *International Journal of Peptide and Protein Research*, 26(1): 92-97 (Jul. 1985).
Alexander et al., "Development of High Potency Universal DR-Restricted Helper Epitopes by Modification of High Affinity DR-Blocking Peptides," *Immunity*, 1: 751-761 (Dec. 1994).
Alves et al., "EphA2 as Target of Anticancer Immunotherapy: Identification of HLS-A*0201-Restricted Epitopes," *Cancer Research*, 63: 8476-8480 (Dec. 1, 2003).
Annex to Form PCT/ISA/206 Communication Relating to the Results of the Partial International Search dated Apr. 3, 2006, in PCT/US2005/033794.
Baca et al., "Chemical Ligation of Cysteine-Containing Peptides: Synthesis of a 22 kDa Tethered Dimer of HIV-1 Protease," *J. Am. Chem. Soc.* 117:1881-1887 (1995).
Bakker et al., "Generation of Antimelanoma Cytotoxic T Lymphocytes from Healthy Donors after Presentation of Melanoma-associated Antigen-derived Epitopes by Dendritic Cells in Vitro," *Cancer Research*, 55: 5330-5334 (Nov. 15, 1995).
Bedrosian et al., "Intranodal Administration of Peptide-Pulsed Mature Dendritic Cell Vaccines Results in Superior CD8+ T-Cell Function in Melanoma Patients," *Journal of Clinical Oncology*, 21(20): 3826-3835 (Oct. 15, 2003).
Berzofsky, "New Strategies for Designing and Optimizing Vaccines," *ASM News*, 70(5): 219-223 (2004).
Bigg et al., "The Mammalian Chitinase-like Lectin, YKL-40, Binds Specifically to Type I Collagen and Modulates the Rate of Type I Collagen Fibril Formation," *The Journal of Biological Chemistry*, 281(30): 21081-21095 (Jul. 28, 2006).
Bigner et al., "Induction of lethal experimental allergic encephalomyelitis in nonhuman primates and guinea pigs with human glioblastoma multiforme tissue," *Journal of Neurosurgery*, 55: 32-42 (Jul. 1981).
Bitter et al., "Expression and Secretion Vectors for Yeast," *Methods in Enzymology, Recombinant DNA*, 153(Part D): 516-544 (1987).
Blanc-Brude et al., "Inhibitor of apoptosis protein survivin regulates vascular injury," *Nature Medicine*, 8(9): 987-994 (Sep. 2002).
Boon, "Toward a Genetic Analysis of Tumor Rejection Antigens," *Advances in Cancer Research*, 58: 177-210 (1992).
Bownds et al., "Induction of Tumor-Reactive Cytotoxic T-Lymphocytes Using a Peptide from NY-ESO-1 Modified at the Carboxy-terminus to Enhance HLA-A2.1 Binding Affinity and Stability in Solution," *Journal of Immunotherapy*, 24(1): 1-9 (Jan./Feb. 2001).
Brantley et al., "Soluble Eph A receptors inhibit tumor angiogenesis and progression in vivo," *Oncogene*, 21(46): 7011-7026 (Oct. 10, 2002).
Buchwald et al., "Long-term, continuous intravenous heparin administration by an implantable infusion pump in ambulatory patients with recurrent venous thrombosis," *Surgery*, 88(4): 507-516 (Oct. 1980).
Butowski et al., "A North American brain tumor consortium phase II study of poly-ICLC for adult patients with recurrent anaplastic gliomas," *J. Neurooncol.*, 91: 183-189 (2009).
Butowski et al., "A phase II clinical trial of poly-ICLC with radiation for adult patients with newly diagnosed supratentorial glioblastoma: a North American Brain Tumor Consortium (NABTC01-05)," *J. Neurooncol.*, 97: 175-182 (2009).
Byers, "What Can Randomized Controlled Trials Tell Us About Nutrition and Cancer Prevention?" *CA—A Cancer Journal for Clinicians*, 49(6): 353-361 (Nov. /Dec. 1999).
Carmon et al., "Characterization of novel breast carcinoma-associated BA46-derived peptides in HLA-A2.1/$D^b$-β2m transgenic mice," *The Journal of Clinical Investigation*, 110(4): 453-462 (Aug. 2002).
Celis, "Overlapping Human Leukocyte Antigen Class I/II Binding Peptide Vaccine for the Treatment of Patients With Stage IV Melanoma," *Cancer*, 110(1): 203-214 (Jul. 1, 2007).
Chen et al., "Identification of NY-ESO-1 Peptide Analogues Capable of Improved Stimulation of Tumor-Reactive CTL," *The Journal of Immunology*, 165(2): 948-955 (Jul. 15, 2000).
Chianese-Bullock et al., "MAGE-A1-, MAGE-A10, and gp100-Derived Peptides Are Immunogenic When Combined with Granulocyte-Macrophage Colony-Stimulating Factor and Montanide ISA-51 Adjuvant and Administered as Part of a Multipeptide Vaccine for Melanoma," *The Journal of Immunology*, 174: 3080-3086 (2005).
Ciesielski et al., "Antitumor cytotoxic T-cell response induced by a surviving peptide mimic," *Cancer Immunol. Immunother.*, 59: 1211-1221 (2010).
Clinical Trial NCT00345163, A Study to Evaluate Bevacizumab Alone or in Combination With Irinotecan for Treatment of Glioblastoma Multiforme (BRAIN), (Jun. 27, 2006).
Cockett et al., "High Level Expression of Tissue Inhibitor or Metalloproteinases in Chinese Hamster Ovary Cells Using Glutamine Synthetase Gene Amplification," *Bio/Technology*, 8(7): 662-667 (Jul. 1990).
Cohen et al., "FDA Drug Approval Summary: Bevacizumab (Avastin®) as Treatment of Recurrent Glioblastoma Multiforme," *The Oncologist*, 14:1131-1138 (2009).
Colbère-Garapin et al., "A New Dominant Hybrid Selective Marker for Higher Eukaryotic Cells," *J. Mol. Biol.*, 150:1-14 (1981).

(56) References Cited

OTHER PUBLICATIONS

Cotterchio et al., "Ontario Familial Colon Cancer Registry: Methods and First-year Response Rates," *Chronic Diseases in Canada*, 21(2): 1-10 (2000).
Crouse et al., "Expression and Amplification of Engineered Mouse Dihydrofolate Reductase Minigenes," *Molecular and Cellular Biology*, 3(2): 257-266 (Feb. 1983).
D' Aoust et al., "Influenza virus-like particles produced by transient expression in Nicotiana benthamiana induce a protective immune response against a lethal viral challenge in mice," *Plant Biotechnology Journal*, 6: 930-940 (2008).
De Vleeschouwer et al., "Postoperative Adjuvant Dendritic Cell-Based Immunotherapy in Patients with Relapsed Glioblastoma Multiforme," *Clinical Cancer Research*, 14(10): 3098-3104 (May 15, 2008).
Debinski et al., "Receptor for interleukin 13 is abundantly and specifically over-expressed in patients with glioblastoma multiforme," *International Journal of Oncology*, 15: 481-486 (1999).
Debinski et al., "Receptor for Interleukin 13 is a Marker and Therapeutic Target for Human High-Grade Gliomas," *Clinical Cancer Research*, 5: 985-990 (May 1999).
Debinski et al., "Expression of a restrictive receptor for interleukin 13 is associated with glial transformation," *Journal of Neuro-Oncology*, 48: 103-111 (2000).
Debinski et al., "Molecular Expression Analysis of Restrictive Receptor for Interleukin 13, a Brain Tumor-associated Cancer/Testis Antigen," *Molecular Medicine*, 6(5): 440-449 (May 2000).
Debinski et al., "EphA2 Receptor Represents a New Marker and Therapeutic Target in Glioblastoma," *Neuro-Oncology*, Abstract GE-02: 336-337 (Oct. 2004).
Eguchi et al., "Identification of Interleukin-13 Receptor α2 Peptide Analogues Capable of Inducing Improved Antiglioma CTL Responses," *Cancer Research*, 66(11): 5883-5891 (Jun. 1, 2006).
European Patent Office, International Search Report dated Jun. 29, 2006, in PCT/US2005/033794.
European Patent Office, Extended European Search Report, in European Patent Application No. 11820530.1 (Jan. 12, 2015).
Fallert et al., "Improved detection of simian immunodeficiency virus RNA by in situ hybridization in fixed tissue sections: combined effects of temperatures for tissue fixation and probe hybridization," *Journal of Virological Methods*, 99: 23-32 (2002).
Fichtner-Feigl et al., "IL-13 signaling through the IL-13α$_2$ receptor is involved in induction of TGF-β$_1$ production and fibrosis," *Nature Medicine*, 12(1): 99-106 (Jan. 2006).
Foecking et al., "Powerful and versatile enhancer-promoter unit for mammalian expression vectors," *Gene* 45: 101-105 (1986).
Francini et al., "High-Affinity HLA-A(*)02.01 Peptides from Parathyroid Hormone-Related Protein Generate In Vitro and In Vivo Antitumor CTL Response Without Autoimmune Side Effects," *The Journal of Immunology*, 169(9): 4840-4849 (Nov. 1, 2002).
Fujita et al., "Effective Immunotherapy against Murine Gliomas Using Type 1 Polarizing Dendritic Cells-Significant Roles of CXCL10," *Cancer Research*, 69(4): 1587-6683 (Feb. 15, 2009).
Gustafson et al., "Therapeutic vaccines for malignant brain tumors," *Biologics: Targets & Therapy*, 2(4): 753-761 (2008).
Gilliet et al., "Intranodal injection of semimature monocyte-derived dendritic cells induces T helper type 1 responses to protein neoantigen," *Blood*, 102(1): 36-42 (Jul. 1, 2003).
Graff-Dubois et al., "Generation of CTL Recognizing an HLA-A*0201-Restricted Epitope Shared by MAGE-A1, -A2, -A3, -A4, -A6, -A10, and -A12 Tumor Antigens: Implication in a Broad-Spectrum Tumor Immunotherapy," *The Journal of Immunology*, 169: 575-580 (2002).
Greenspan et al., "Defining epitopes: It's not as easy as it seems," *Nature Biotechnology*, 17: 936-937 (Oct. 1999).
Greten et al., "Peptide-β2-microglobulin-MHC fusion molecules bind antigen-specific T cells and can be used for multivalent MHC-Ig complexes," *Journal of Immunological Methods*, 271:125-135 (2002).
Gross et al., "High vaccination efficiency of low-affinity epitopes in antitumor immunotherapy," *The Journal of Clinical Investigation*, 113(3): 425-433 (Feb. 2004).
Gura, "Cancer Models, Systems for Identifying New Drugs Are Often Faulty," *Science*, 278: 1041-1042 (Nov. 7, 1997).
Hatano et al., "Vaccination with EphA2-derived T cell-epitopes promotes immunity against both EphA2-expressing and EphA2-negative tumors," *Journal of Translational Medicine*, 2(40): 1-9 (2004).
Hatano et al., "EphA2 as a Glioma-Associated Antigen: A Novel Target for Glioma Vaccines," *Neoplasia*, 7(8): 717-722 (Aug. 2005).
Herrem et al., "Expression EphA2 is Prognostic of Disease-Free Interval and Overall Survival in Surgically Treated Patients with Renal Cell Carcinoma," *Clinical Cancer Research*, 11(1): 226-231 (Jan. 1, 2005).
Inouye et al., "Up-promoter mutations in the Ipp gene *Escherichia coli*," *Nucleic Acids Research*, 13(9): 3101-3110 (1985).
International Bureau of WIPO, International Preliminary Report on Patentability, dated Apr. 5, 2007, in PCT/US2005/033794.
International Bureau of WIPO, International Preliminary Report on Patentability in International Patent Application No. PCT/US2011/048823 (Mar. 7, 2013).
Izumoto et al., "Phase II clinical trial of Wilms tumor 1 peptide vaccination for patients with recurrent glioblastoma multiforme," *J. Neurosurg.*, 108: 963-971 (May 2008).
Izumoto, "Immunotherapy of Glioma—focusing on WT1 peptide vaccine therapy," *No Shinkei Geka Sokuho*, 19(2): 170-177 (2009).
Japanese Patent Office, Notice of Reasons for Refusal, dated Jul. 7, 2015, in Japanese Patent Application No. 526099/2013.
Japanese Patent Office, Notice of Reasons for Refusal, dated Jun. 6, 2017, in Japanese Application No. 139885/2016.
Japanese Patent Office, Notice of Reasons for Refusal, dated Jun. 12, 2018, in Japanese Application No. 139885/2016.
Kaiser, "First Pass at Cancer Genome Reveals Complex Landscape," *Science*, 313: 1370 (Sep. 8, 2006).
Kaliński et al., "IL-12-Deficient Dendritic Cells, Generated in the Presence of Prostaglandin E$_2$, Promote Type 2 Cytokine Production in Maturing Human Naïve T Helper Cells," *The Journal of Immunology*, 159(1): 28-35 (Jul. 1, 1997).
Kaliński et al., "Final Maturation of Dendritic Cells is Associated with Impaired Responsiveness to IFN-γ and to Bacterial IL-12 Inducers: Decreased Ability of Mature Dendritic Cells to Produce IL-12 During the Interaction with Th Cells," *The Journal of Immunology*, 162(6): 3231-3236 (Mar. 15, 1999).
Kalinski et al., "Polarized Dendritic Cells as Cancer Vaccines: Directing Effector-type T Cells to Tumors," *Semin. Immunol.*, 22(3): 173-182 (Jun. 2010).
Kamber et al., "The Synthesis of Cystine Peptides by Iodine Oxidation of S-Trityl-cysteine and S-Acetamidomethyl-cysteine Peptides," *Helvetica Chimica Acta*, 63(4): 899-915 (1980).
Kikuchi et al., "Vaccination of Glioma Patients with Fusions of Dendritic and Glioma Cells and Recombinant Human Interleukin 12," *J. Immunother*, 27(6): 452-459 (Nov./Dec. 2004).
Kinch et al., "Overexpression and functional alterations of the EphA2 tyrosine kinase in cancer," *Clinical & Experimental Metastasis*, 20: 59-68 (2003).
Kirkin et al., "Melanoma-associated antigens recognized by cytotoxic T lymphocytes," *APMIS*, 106: 665-679 (1998).
Kirkwood et al., "Immunogenicity and Antitumor Effects of Vaccination with Peptide Vaccine +/− Granulocyte-Monocyte Colony-Stimulating Factor and/or IFN-α2b in Advanced Metastatic Melanoma: Eastern Cooperative Oncology Group Phase II Trial E1696," *Clinical Cancer Research*, 15(4): 1443-1451 (Feb. 15, 2009).
Koch et al., "An abundant ubiquitous glycoprotein (GP$_{100}$) in nucleated mammalian cells," *FEBS Letters*, 179(2): 294-298 (Jan. 1985).
Korean Intellectual Property Office, International Search Report-Written Opinion dated Apr. 27, 2012, in PCT/US2011/048823.
Kouklis et al., "In vitro assembly properties of vimentin mutagenized at the β-site tail motif," *Journal of Cell Science*, 106(Pt.3): 919-928 (1993).

(56) References Cited

OTHER PUBLICATIONS

Krug et al., "WT1 peptide vaccinations induce CD4 and CD8 T cell immune responses in patients with mesothelioma and non-small cell lung cancer," *Cancer Immuno. Ther.*, 59(10): 1467-1479 (2010).
Liau et al., "Dendritic Cell Vaccination in Glioblastoma Patients Induces Systemic and Intracranial T-cell Responses Modulated by the Local Central Nervous System Tumor Microenvironment," *Clinical Cancer Research*, 11(15): 5515-5525 (Aug. 1, 2005).
Liu et al., Chemical Ligation Approach to Form a Peptide Bond between Unprotected Peptide Segments. Concept and Model Study, *Journal of the American Chemical Society*, 116(10): 4149-4153 (May 18, 1994).
Liu et al., "Peptide segment ligation strategy without use of protecting groups," *Proc. Natl. Acad. Sci. USA*, 91:6584-6588 (Jul. 1994).
Liu et al., "Acyl Disulfide-Mediated Intramolecular Acylation for Orthogonal Coupling Between Unprotected Peptide Segments, Mechanism and Application," *Tetrahedron Letters*, 37(7): 933-936 (1996).
Liu et al., "HER-2, gp100, and MAGE-1 Are Expressed in Human Glioblastoma and Recognized by Cytotoxic T Cells," *Cancer Research*, 64: 4980-4986 (Jul. 15, 2004).
Liu et al., "A Genome-Wide Screen Reveals Functional Gene Clusters in the Cancer Genome and Identified EphA2 as a Mitogen in Glioblastoma," *Cancer Research*, 66:10815-10823 (2006).
Livak et al., "Analysis of Relative Gene Expression Data Using Real-Time Quantitative PCR and the 2-$\Delta\Delta C_T$ Method," *Methods*, 25: 402-408 (2001).
Logan et al., "Adenovirus tripartite leader sequence enhances translation of mRNAs late after infection," *Proc. Natl. Acad. Sci. USA*, 81: 3655-3659 (Jun. 1984).
Lupetti et al., "Translation of a Retained Intron in Tyrosinase-related Protein (TRP) 2 mRNA Generates a New Cytotoxic T Lymphocyte (CTL)-defined and Shared Human Melanoma Antigen Not Expressed in Normal Cells of the Melanocytic Lineage," *The Journal of Experimental Medicine*, 188(6): 1005-1016 (Sep. 21, 1998).
Mailliard et al., "α-Type-1 Polarized Dendritic Cells: A Novel Immunization Tool with Optimized CTL-inducing Activity," *Cancer Research*, 64(17): 5934-5937 (Sep. 1, 2004).
Marincola et al., "Tumors as elusive targets of T-cell-based active immunotherapy," *Trends in Immunology*, 24(6): 334-341 (Jun. 2003).
Merck Source, "Vaccine" *Dorland's Illustrated Medical Dictionary*, (2007).
Monsurrò et al., Functional Heterogeneity of Vaccine-Induced $CD8^+$ T Cells, *The Journal of Immunology*, 168: 5933-5942 (2002).
Muthuswamy et al., "Ability of Mature Dendritic Cells to Interact with Regulatory T Cells is Imprinted during Maturation," *Cancer Research*, 68(14): 5972-5978 (Jul. 15, 2008).
Nakagawa et al., "The Use of Polymer-Bound Oximes for the Synthesis of Large Peptides Usable in Segment Condensation: Synthesis of a 44 Amino Acid Amphiphilic Peptide Model of Apolipoprotein A-1," *J. Am. Chem. Soc.*, 107(24): 7087-7092 (1985).
Naruse-Nakajima et al., "Involvement of EphA2 in the formation of the tail notochord via interaction with ephrinA1," *Mechanisms of Development*, 102: 95-105 (2001).
Neeson et al., "Effects of the Tumor Microenvironment on the Efficacy of Tumor Immunotherapy," *Immunological Investigations*, 35: 359-394 (2006).
Nishimura et al., "Adoptive Transfer of Type 1 CTL Mediates Effective Anti-Central Nervous System Tumor Response: Critical Roles of IFN-Inducible Protein-10," *Cancer Research*, 66(8): 4478-4487 (Apr. 15, 2006).
Nutt et al., "YKL-40 is a Differential Diagnostic Marker for Histologic Subtypes of High-Grade Gliomas," *Clinical Cancer Research*, 11:2258-2264 (Mar. 15, 2005).
O'Connell et al., "Elucidating the elite: mechanisms of control in HIV-1 infection," *Trends in Pharmacological Sciences*, 30(12): 631-637 (2009).
Ogawa et al., "The ephrin-A1 ligand and its receptor, EphA2, are expressed during tumor neovascularization," *Oncogene*, 19(52): 6043-6052 (Dec. 7, 2000).
Ogden et al., "Defective Receptor Expression and Dendritic Cell Differentiation of Monocytes in Glioblastomas," *Neurosurgery*, 59(4): 902-910 (Oct. 2006).
Okada et al., "Bone Marrow-Derived Dendritic Cells Pulsed with a Tumor-specific peptide elicit effective Anti-Tumor Immunity Against Intercranial Neoplasms," *International Journal of Cancer*, 78(1): 196-201 (Sep. 25, 1998).
Okada et al., "Gene Therapy of Malignant Gliomas: A Pilot Study of Vaccination with Irradiated Autologous Glioma and Dendritic Cells Admixed with IL-4 Transduced Fibroblasts to Elicit an Immune Response," *Human Gene Therapy*, 12(5): 575-595 (Mar. 20, 2001).
Okada et al., "Cytokine gene therapy of gliomas: effective induction of therapeutic immunity to intracranial tumors by peripheral immunization with interleukin-4 transduced glioma cells," *Gene Therapy*, 8(15): 1157-1166 (Aug. 2001).
Okada et al., "Autologous glioma cell vaccine admixed with interleukin-4 gene transfected fibroblasts in the treatment of recurrent glioblastoma: preliminary observations in a patient with a favorable response to therapy," *Journal of Neuro-Oncology*, 64(1-2): 13-20 (Aug./Sep. 2003).
Okada et al., "Autologous glioma cell vaccine admixed with interleukin-4 gene transfected fibroblasts in the treatment of patients with malignant gliomas," *Journal of Translational Medicine*, 5(67): 1-10 (2007).
Okada et al., "Expression of glioma-associated antigens in pediatric brain stem and non-brain stem gliomas," *J. Neurooncol.*, 88(3): 245-250 (Jul. 2008).
Okada et al., "Immunotherapeutic Approaches for Glioma," *Crit. Rev. Immunol.*, 29(1): 1-42 (2009).
Okada et al., "Type 1 Dendritic Cell (DC) Vaccines in Combination with Poly-ICLC in Participants with Recurrent Malignant Glioma," *Neuro-Oncology*, 11(2), Abstract No. New 14: 224 (Apr. 2009).
Okada et al., "Type-1 Dendritic Cell Vaccines in Combination with Poly-ICLC-Association Between Positive Tetramer Response and 6-Month Progression-Free Survival," *Neuro-Oncology*, 11(5) Abstract No. 207:611 (Oct. 2009).
Okada et al., "Type 1 Dendritic Cell Vaccines in Combination with Poly-ICLC-Association Between Positive Tetramer Response and 6-Month Progression-Free Survival," *Neuro-Oncology*, 11(6) Abstract No. 029:883 (Dec. 2009).
Okada et al., "Type-1 dendritic cell vaccines in combination with poly-ICLC-association between positive tetramer response and 6-month progression-free survival in patients with recurrent malignant glioma," *Cancer Research*, 70(8) Abstract No. 4754: (Apr. 15, 2010).
Okada et al., "Induction of Robust Type-I $CD8^+$ T-cell Responses in WHO Grade 2 Low-Grade Glioma Patients Receiving Peptide-Based Vaccines in Combination with Poly-ICLC," *Clinical Cancer Research*, 21(2): 286-294 (Jan. 15, 2015).
Okano et al., "Identification of a Novel HLA-A*2010-restricted, Cytotoxic T Lymphocyte Epitope in a Human Glioma-associated Antigen, Interleukin 13 Receptor α2 Chain," *Clinical Cancer Research*, 8(9): 2851-2855 (Sep. 2002).
Okano et al., "Correction, Identification of a Novel HLA-A*2010-restricted, Cytotoxic T Lymphocyte Epitope in a Human Glioma-associated Antigen, Interleukin 13 Receptor α2 Chain," *Clinical Cancer Research*, 12(11): 3552 (Jun. 1, 2006).
Otto et al., "Lack of toxicity of therapy-induced T cell responses against the universal tumour antigen survivin," *Vaccine*, 23: 884-889 (2005).
Pascolo et al., "HLA-A2.1-restricted Education and Cytolytic Activity of $CD8^+$ T Lymphocytes from β2 Microglobulin (β2m) HLA-A2.1 Monochain Transgenic H-$2D^b$ β2m Double Knockout Mice," *The Journal of Experimental Medicine*, 185(12): 2043-2051 (Jun. 16, 1997).
Pelloski et al., "YKL-40 Expression is Associated with Poorer Response to Radiation and Shorter Overall Survival in Glioblastoma," *Clinical Cancer Research*, 11(9): 3326-3334 (May 1, 2005).
Pennington et al., "Comparison of folding procedures on synthetic ω-conotoxin," *Peptides 1990, Proceedings of the Twenty-First*

(56) References Cited

OTHER PUBLICATIONS

*European Peptide Symposium*, (Giralt et al., eds) (Platja d'Aro, Spain) (Sep. 2-8, 1990) (164-166).

Pollack et al., Expression of p53 and Prognosis in Children with Malignant Gliomas,: *The New England Journal of Medicine*, 346(6): 420-427 (Feb. 7, 2002).

Pollack et al., "Antigen-Specific Immune Responses and Clinical Outcome After Vaccination With Glioma-Associated Antigen Peptides and Polyinosinic-Polycytidylic Acid Stabilized by Lysine and Carboxymethylcellulose in Children With Newly Diagnosed Malignant Brainstem and Nonbrainstem Gliomas," *Journal of Clinical Oncology*, 32(19): 2050-2058 (Jul. 1, 2014).

Pollack, "HLA-A2-Restricted Glioma Antigen-Peptides Vaccinations With Poly-ICLC for Recurrent WHO Grade II Gliomas," Clinical Trials NCT00874861 from ClinicalTrials.gov (first received Apr. 2, 2009; last updated Dec. 8, 2015).

Pollack et al., "Antigen-specific immunoreactivity and clinical outcome following vaccination with glioma-associated antigen peptides in children with recurrent high-grade gliomas: results of a pilot study," *J Neurooncol.*, 130: 517-527 (2016).

Pollack et al., "Immune responses and outcome after vaccination with glioma-associated antigen peptides and poly-ICLC in a pilot study for pediatric recurrent low-grade gliomas," *Neuro-Oncol.*, pp. 1157-1168 (2016).

Prosecution history of U.S. Appl. No. 11/231,618, filed Sep. 21, 2005, current as of Jun. 4, 2014.

Prosecution history of U.S. Appl. No. 12/561,973, filed Sep. 17, 2009, current as of Sep. 5, 2014.

Prosecution history of U.S. Appl. No. 13/215,938, filed Aug. 23, 2011, current as of Nov. 22, 2013.

Prosecution history of U.S. Appl. No. 13/925,093, filed Jun. 24, 2013, current as of May 19, 2014.

Rasala et al., "Production of therapeutic proteins in algae, analysis of expression of seven human proteins in the chloroplast of Chlamydomonas reinhardtii," *Plant Biotechnology Journal*, 8: 719-733 (2010).

Riker et al., "Immune selection after antigen-specific immunotherapy of melanoma," *Surgery*, 126(1): 112-120 (Jul. 1999).

Rodrigues et al., "Normal human monocytes exposed to glioma cells acquire myeloid-derived suppressor cell-like properties," *Neuro-Oncology*, 12(4): 351-365 (Apr. 2010).

Rüther et al., "Easy identification of cDNA clones," *The EMBO Journal*, 2(10): 1791-1794 (1983).

Saikali et al., "Expression of nine tumour antigens in a series of human glioblastoma multiforme: interest of EGFRvIII, IL-13Rα2, gp100 and TRP-2 for immunotherapy," *J. Neurooncol.* 81:139-148 (2007).

Sainio et al., "Differential regulation of two sets of mesonephric tubules by WT-1," *Development*, 124: 1293-1299 (1997).

Salazar et al., "Long-term Treatment of Malignant Gliomas with Intramuscularly Administered Polyinosinic-Polycytidylic Acid Stabilized with Polylysine and Carboxymethylcellulose: An Open Pilot Study," *Neurosurgery*, 38(6): 1096-1104 (Jun. 1996).

Salgaller et al., "Immunization against Epitopes in the Human Melanoma Antigen gp100 following Patient Immunization with Synthetic Peptides," *Cancer Research*, 56: 4749-4757 (Oct. 15, 1996).

Sampson et al., "An epidermal growth factor receptor variant III-targeted vaccine is safe and immunogenic in patients with glioblastoma multiforme," *Molecular Cancer Therapeutics*, 8(10): 2773-2779 (Oct. 2009).

Sasaki et al., "Preferential Expression of Very Late Antigen-4 on Type 1 CTL Cells Plays a Critical Role in Trafficking into Central Nervous System Tumors," *Cancer Research*, 67(13): 6451-6458 (Jul. 1, 2007).

Saudek et al., "A Preliminary Trial of the Programmable Implantable Medication System for Insulin Delivery," *New England Journal of Medicine*, 321(9): 574-579 (Aug. 31, 1989).

Scardino et al., "HER-2/neu and hTERT Cryptic Epitopes as Novel Targets for Broad Spectrum Tumor Immunotherapy," *The Journal of Immunology*, 169: 5900-5906 (2002).

Schnölzer et al., "Constructing Proteins by Dovetailing Unprotected Synthetic Peptides: Backbone-Engineered HIV Protease," *Science*, 256(5054): 221-225 (Apr. 10, 1992).

Schreier et al., "Allotypic differences in murine μ genes," *Nucleic Acids Research*, 74(5): 2381-2389 (1986).

Sefton et al., "Implantable Pumps," *CRC Critical Reviews in Biomedical Engineering*, 14(3): 201-240 (1987).

Sherman et al., "Strategies for Tumor Elimination by Cytotoxic T Lymphocytes," *Critical Reviews in Immunology*, 18: 47-54 (1998).

Shoji et al., "Plant-expressed HA as a seasonal influenza vaccine candidate," *Vaccine*, 26: 2930-2934 (2008).

Slingluff et al., "Helper T-Cell Responses and Clinical Activity of a Melanoma Vaccine With Multiple Peptides From MAGE and Melanocytic Differentiation Antigens," *Journal of Clinical Oncology*, 26(30): 4973-4980 (Oct. 20, 2008).

Smith, "Cancer and the Immune System," *Clinical Immunology*, 14(4): 841-849 (Aug. 1994).

Smith et al., "PTEN Mutation, EGFR Amplification, and Outcome in Patients With Anaplastic Astrocytoma and Glioblastoma Multiforme," *Journal of the National Cancer Institute*, 93(16): 1246-1256 (Aug. 15, 2001).

Stoute et al., "A Preliminary Evaluation of a Recombinant Circumsporozoite Protein Vaccine Against Plasmodium Falciparum Malaria," *The New England Journal of Medicine*, 336(2): 86-91 (Jan. 9, 1997).

Szczepanski et al., "Triggering of Toll-like Receptor 4 Expressed on Human Head and Neck Squamous Cell Carcinoma Promotes Tumor Development and Protects the Tumor from Immune Attack," *Cancer Research*, 69(7): 3105-3113 (Apr. 1, 2009).

Takahashi, T., "Introduction of T Cell-Based Cancer Immunotherapy, Cancer Vaccine and Adoptive T Cell Transfer," *Aichi Cancer Center Research Institute* 19(1): 15-27 (2005).

Tam et al., "Improved Synthesis of 4-(Boc-aminoacyloxymethyl)-phenylacetic Acids for use in Solid Phase Peptide Synthesis," *Synthesis*, 955-957 (Dec. 1979).

Tam et al., "Specificity and formation of unusual amino acids of an amide ligation strategy for unprotected peptides," *International Journal of Peptide & Protein Research*, 45(3): 209-216 (Mar. 1995).

Tatsumi et al., "Disease Stage Variation in CD4+ and CD8+ T-Cell Reactivity to the Receptor Tyrosine Kinase EphA2 in Patients with Renal Cell Carcinoma," *Cancer Research*, 63: 4481-4489 (Aug. 1, 2003).

Van Heeke et al., "Expression of Human Asparagine Synthetase in *Escherichia coli*," *The Journal of Biological Chemistry*, 264(10): 5503-5509 (Apr. 5, 1989).

Vredenburgh et al., "Phase II Trial of Bevacizumab and Irinotecan in Recurrent Malignant Glioma," *Clinical Cancer Research*, 13(4): 1253-1259 (Feb. 15, 2007).

Vredenburgh et al., "Bevacizumab Plus Irinotecan in Recurrent Glioblastoma Multiforme," *Journal of Clinical Oncology*, 25(30): 4722-4729 (Oct. 20, 2007).

Watchmaker et al., "Independent Regulation of Chemokine Responsiveness and Cytolytic Function versus CD8+ T Cell Expansion by Dendritic Cells," *The Journal of Immunology*, 784: 591-597 (2010).

Weber et al., "Phase 1 Trial of Intranodal Injection of a Melan-A/MART-1 DNA Plasmid Vaccine in Patients With Stage IV Melanoma," *J. Immunother.*, 31(2): 215-223 (Feb./Mar. 2008).

Wen et al., "Malignant Gliomas," *Neurology and Neuroscience Reports*, 4(3): 218-227 (May 2004).

Wheeler et al., "Vaccination Elicits Correlated Immune and Clinical Responses in Glioblastoma Multiforme Patients," *Cancer Research*, 68(14): 5955-5964 (Jul. 15, 2008).

Yajima et al., "Immunologic Evaluation of Personalized Peptide Vaccination for Patients with Advanced Malignant Glioma," *Clin. Cancer Res.*, 11(16): 5900-5911 (2005).

Yamanaka et al., "Clinical Evaluation of Dendritic Cell Vaccination for Patients with Recurrent Glioma: Results of a Clinical Phase I/II Trial," *Clinical Cancer Research*, 11(11): 4160-4167 (Jun. 1, 2005).

Yamanaka et al., "Peptide-based immunotherapeutic approaches to glioma: a review," *Expert Opin. Biol. Ther.* 7(5): 645-649 (2007).

(56) References Cited

OTHER PUBLICATIONS

Yamashiro et al., "New segment synthesis of α-inhibin-92 by the acyl disulfide method," *Int. J. Peptide Protein Res.*, 31(3): 322-334 (Mar. 1988).
Yu et al., "Vaccination with Tumor Lysate-Pulsed Dendritic Cells Elicits Antigen-Specific, Cytotoxic T-Cells in Patients with Malignant Glioma," *Cancer Research*, 64(14): 4973-4979 (Jul. 15, 2004).
Zelinski et al., "EphA2 Overexpression Causes Tumorigenesis of Mammary Epithelial Cells," *Cancer Research*, 67: 2301-2306 (Mar. 1, 2001).
Zhang et al., "Antigenic Profiling of Glioma Cells to Generate Allogeneic Vaccines or Dendritic Cell-Based Therapeutics," *Clin. Cancer Res.* 13(2): 566-575 (Jan. 15, 2007).
Zhu et al., "Toll like receptor-3 ligand poly-ICLC promotes the efficacy of peripheral vaccinations with tumor antigen-derived peptide epitopes in murine CNS tumor models," *Journal of Translational Medicine*, 5(10): 1-15 (Feb. 12, 2007).
Zhu et al., "Poly-ICLC promotes the infiltration of effector T cells into intracranial gliomas via induction of CXCL10 in IFN-α and IFN-γ dependent manners," *Cancer Immunol. Immunother.* 59:1401-1409 (2010).
Wierecky et al., "Immunologic and Clinical Responses after Vaccinations with Peptide-Pulsed Dendritic Cells in Metastatic Renal Cancer Patients", *Cancer Research*, vol. 66(11), pp. 5910-5918 (2006).
U.S. Appl. No. 11/231,618, filed Sep. 21, 2005.
U.S. Appl. No. 12/561,973, filed Sep. 17, 2009.
U.S. Appl. No. 13/215,938, filed Aug. 23, 2011.
U.S. Appl. No. 13/925,093, filed Jun. 24, 2013.
U.S. Appl. No. 14/478,458, filed Sep. 5, 2014.
U.S. Appl. No. 14/515,939, filed Oct. 16, 2014.
U.S. Appl. No. 14/688,376, filed Apr. 16, 2015.
U.S. Appl. No. 14/724,127, filed May 28, 2015.
U.S. Appl. No. 14/951,821, filed Nov. 25, 2015.
U.S. Appl. No. 15/205,203, filed Jul. 8, 2016.
U.S. Appl. No. 17/109,463, filed Dec. 2, 2020.
European Patent Office, Extended European Search Report issued in counterpart European Patent Application No. 22193769.1, dated Mar. 3, 2023.
Jiang et al., "HLA Tetramer—Based Artificial Antigen-Presenting Cells Efficiently Stimulate CTLs Specific for Malignant Glioma", *Clinical Cancer Research*, 13(24): 7329-7334 (2007).

\* cited by examiner

PEPTIDE ANALOGS CAPABLE OF ENHANCING STIMULATION OF A GLIOMA-SPECIFIC CTL RESPONSE

CROSS-REFERENCE TO RELATED APPLICATIONS

This patent application is a continuation of co-pending U.S. application Ser. No. 15/205,203, now U.S. Pat. No. 10,434,155, which was filed on Jul. 8, 2016, which is a continuation of U.S. application Ser. No. 14/951,821, which was filed on Nov. 25, 2015, now abandoned, which is a continuation of U.S. patent application Ser. No. 14/688,376, which was filed on Apr. 16, 2015, now abandoned, which is a continuation of U.S. patent application Ser. No. 14/478,458, which was filed on Sep. 5, 2014, now abandoned, which is a continuation of U.S. patent application Ser. No. 12/561,973, now U.S. Pat. No. 8,859,488, which was filed on Sep. 17, 2009, which is a continuation of U.S. patent application Ser. No. 11/231,618, now U.S. Pat. No. 7,612,162, which was filed on Sep. 21, 2005, and which claims the benefit of U.S. Provisional Patent Application No. 60/611,797 filed Sep. 21, 2004, the disclosure of each of which is incorporated by reference herein in its entirety.

STATEMENT REGARDING FEDERALLY SPONSORED RESEARCH OR DEVELOPMENT

This invention was made with government support under Grant Numbers CA117152 and NS040923 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,228 Byte ASCII (Text) file named "725951_ST25.TXT," dated Jul. 7, 2016.

FIELD OF INVENTION

The invention pertains to reagents and methods for treatment of glioma.

BACKGROUND OF THE INVENTION

Brain tumors are particularly difficult to treat using conventional methods such as surgery, radiotherapy, or chemotherapy. Factors such as invasive growth patterns and the blood-brain barrier make the treatment of malignant gliomas more problematic than other tumors. The lack of effective treatment options for patients has led to the development of alternative therapies, such as immunotherapy.

Immunotherapy is a promising new approach in the treatment of malignant gliomas. The efficacy of peripheral immunizations with autologous glioma cells or dendritic cells (DC) pulsed with synthetic peptides for tumor-antigen-specific T cell epitopes has been demonstrated in preclinical mouse models (Okada et al., 2001; Okada et al., 1998). Specific T cell epitope-based vaccines are likely safer than whole glioma cell-based vaccines due to the lack of theoretical autoimmune responses against normal brain components. Such antigen-specific approaches may also be more effective than the bulk tumor-antigen approaches because presentation of immunogenic T cell-epitopes and stimulation of antigen-specific T cell precursors can take place more efficiently with the use of specific antigen-peptides than bulk tumor antigens.

The identification of T cell immuno-epitopes in human glioma associated antigens is required for the development of such vaccines against human gliomas. Few cytotoxic T lymphocyte (CTL) immuno-epitopes have been identified for human malignant gliomas. However, an HLA (human leukocyte antigen)-A2-restricted cytotoxic T lymphocyte (CTL) epitope derived from the interleukin (IL)-13 receptor (R) α2 was recently identified (Okano et al., 2002). IL-13Rα2 is known to be expressed in the majority of human malignant gliomas but not in normal tissues (Debinski et al., 2000), thus making the identified epitope (IL-13Rα2$_{345-353}$) an attractive component of peptide-based vaccines for gliomas. By generating unique CTL lines by stimulation of CD8+ cells with the peptide IL-13Rα2$_{345-353}$, it was demonstrated that IL-13Rα2 positive, HLA-A2 positive glioma cells were efficiently lysed in an antigen-specific manner. However, it remains unclear how efficiently such peptide-based vaccines can induce specific CTLs and whether peptide-analogues can be used for optimal expansion and activation of IL-13Rα2 specific HLA-A2-restricted CTL.

It has been demonstrated that certain amino acid substitutions in peptides identified as CTL epitopes could greatly enhance the binding affinity of such peptides to the HLA (human leukocyte antigen) complex and thus would augment the immunogenicity of the peptide (Bownds et al., 2001; Chen et al., 2000). The enhancement of the immunogenicity of IL-13Rα2$_{345-353}$, and other such epitopes could lead to the development of powerful, tumor-specific peptide-based vaccines, which would be a significant improvement in the current treatment regime for malignant gliomas. However, there remains a need for an improved polypeptide HLA-A2-restricted cytotoxic T lymphocyte (CTL) epitope.

As discussed above, few cytotoxic T lymphocyte (CTL) immuno-epitopes have been identified for human malignant gliomas. Given the marked antigenic heterogeneity of gliomas, however, immunotherapy with a single tumor-specific T-cell epitope might merely promote transient stabilization of disease, prior to the progression of antigen loss variants. EphA2 is a member of the Eph family of receptor tyrosine kinases, comprised of two major classes (EphA and EphB), which are distinguished by their specificities for ligands (ephrin-A and ephrin-B, respectively). EphA2 is frequently overexpressed and often functionally dysregulated in advanced cancers, such as metastatic lesions (Kinch et al., 2003). Due to the aggressive and invasive nature of malignant gliomas, EphA2 might be expressed in this tumor entity and could be a potential target for glioma vaccines. T-cell immunoepitopes in EphA2 have been identified and characterized as potential targets and surrogate markers for other forms of cancer immunotherapy (Alves et al., 2003, and Tatsumi et al., 2003, the disclosures of which are incorporated by reference herein). The identification of additional CTL epitopes is a necessary step in the development of multiepitope-based vaccines for glioma which would be a significant improvement in the current treatment regime for malignant gliomas.

BRIEF SUMMARY OF THE INVENTION

The invention provides a peptide derived from IL-13Rα2, which serves as a HLA-A2-restricted cytotoxic T lymphocyte (CTL) epitope. The inventive peptide can comprise, consist of, or consist essentially of a substitution mutant variant of WLPFGFILI (SEQ ID NO:1), where least at one of the amino acid residues can be substituted for an amino acid other than the indicated residue. In addition, the inventive peptide can comprise, consist of, or consist essentially of any of the following sequences: WLPFGFILV (SEQ ID NO:2), ALPFGFILV (SEQ ID NO:3), or ELPFGFILV (SEQ ID NO:4). The invention also provides a use of any of the above peptides as a vaccine for glioma. In addition, the invention provides a method of vaccinating a patient against glioma, where the peptide is introduced into a patient under conditions sufficient for the patient to develop a CTL response. Further, the invention provides a use of a peptide having the sequence TLADFDPRV (SEQ ID NO:6) or a composition comprising said peptide and a physiologically acceptable carrier, as a vaccine for glioma. The invention also provides a method of vaccinating a patient against glioma, where a peptide having the sequence TLADFDPRV (SEQ ID NO:6) or a composition comprising said peptide and a physiologically acceptable carrier, is introduced into a patient under conditions sufficient for the patient to develop a CTL response. These and other advantages of the invention, as well as additional inventive features, will be apparent from the accompanying drawings and the description of the invention provided herein.

Figure 1:
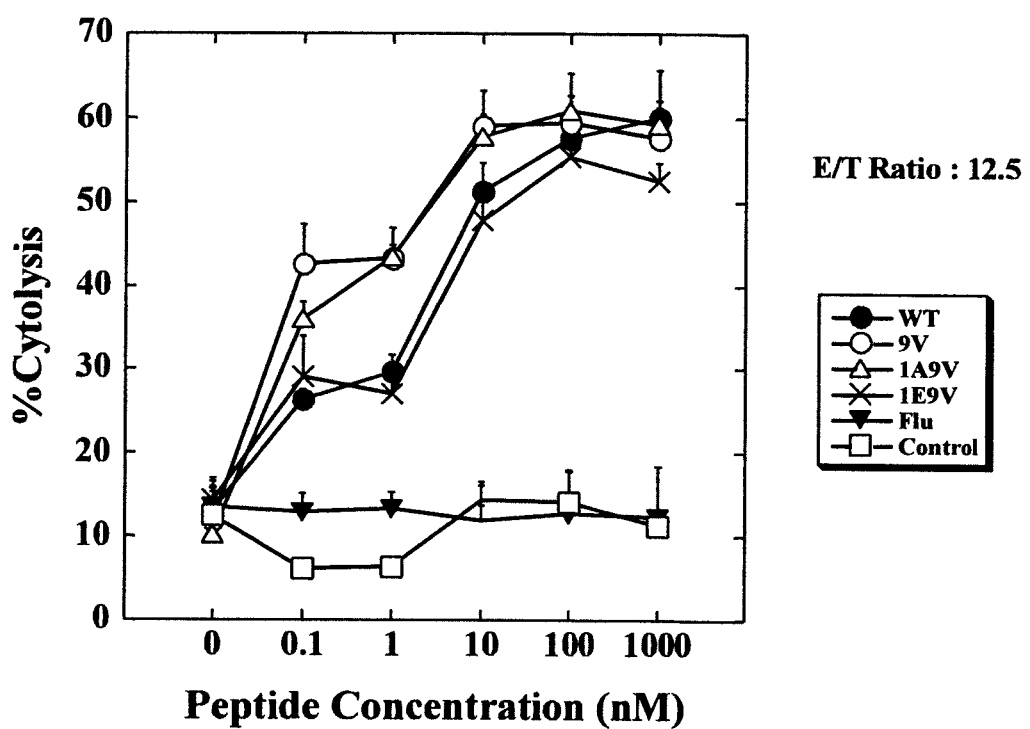
FIG. 1 graphically presents data demonstrating that IL-13Rα2-V9 and IL-13Rα2-A1V9 induced a higher magnitude of CTL reactivity than the native IL-13Rα2$_{345\text{-}353}$ or IL-13Rα2-E1V9 against T2 cells loaded with various concentrations of native IL-13Rα2$_{345\text{-}353}$. CD8+ T cells from an HLA-A2+ glioma patient were stimulated with DCs loaded with either native IL-13Rα2$_{345\text{-}353}$ (●), IL-13Rα2-V9 (○), IL-13Rα2-A1V9 (Δ), IL-13Rα2-E1V9 (X), Influenza M1$_{58\text{-}66}$ peptide (▼), or no peptide (□) for 10 days. Then, the T cells were tested for lytic activity against T2 cells loaded with indicated concentrations of IL-13Rα2$_{345\text{-}353}$ or no peptide by 4-hr $^{51}$Cr-release assay. The E/T ratio was 12.5. $P<0.01$ for IL-13Rα2-V9 vs. native as well as IL-13Rα2-A1V9 vs. native at 0.1 and 1 nM by two-tailed Student-t test. These data demonstrate results from one of three separate experiments with similar results.

(HLA-A2+, EphA2+), U251 (HLA-A2+, EphA2+) and A172 (HLA-A2−, EphA2+) by 4-hr $^{51}$Cr-release assay.

DETAILED DESCRIPTION OF THE INVENTION

In one embodiment, the invention provides an isolated peptide that comprises, consists of, or consists essentially of an amino acid sequence comprising, consisting of, or consisting essentially of a substitution mutant variant of WLPFGFILI (SEQ ID NO:1), wherein at least one of the amino acid residues in SEQ ID NO:1 is substituted with an amino acid other than the indicated residue. For example, at least two (e.g., three or more, four or more, etc.) of the amino acid residues in SEQ ID NO:1 can be substituted with an amino acid other than the indicated residue. Preferably, however, the inventive polypeptide contains a substitution of only one or two of the amino acids. Moreover, while the inventive polypeptide can comprise such a sequence of amino acids, more preferably, the inventive polypeptide consists essentially of such a sequence, and even more preferably, the inventive polypeptide consists of such sequence (i.e., such that the inventive polypeptide consists of nine amino acids).

The substitution from SEQ ID NO:1 can be, but need not be, a conservative substitution. Conservative substitutions are well known in the art and can be amino acid replacements that preserve the structure and functional properties of proteins, such as the substitution of one or more amino acids by similar amino acids. For example, a conservative substitution can be the substitution of an amino acid for another amino acid within the same general class (e.g., an acidic amino acid, a basic amino acid, or a neutral amino acid).

Preferred embodiments of the inventive peptide include substituting the W in the first position of SEQ ID NO:1 with an amino acid other than W, substituting the I in the ninth position of SEQ ID NO:1 with an amino acid other than I, or any combination thereof. For example, the W in the first position of SEQ ID NO:1 can be substituted with either A or E, and/or the I in the ninth position of SEQ ID NO:1 can be substituted with V. Preferred examples of the inventive peptide include isolated peptides comprising, consisting of, or consisting essentially of a sequence of amino acid residues comprising, consisting of, or consisting essentially of WLPFGFILV (SEQ ID NO:2), ALPFGFILV (SEQ ID NO:3), or ELPFGFILV (SEQ ID NO:4).

The inventive peptide can be prepared by methods known to those of ordinary skill in the art. For example, the inventive peptide can be synthesized using solid phase peptide synthesis techniques (e.g., Fmoc). Alternatively, the peptide can be synthesized using recombinant DNA technology (e.g., using bacterial or eukaryotic expression systems). Accordingly, to facilitate such methods, the invention provides genetic vectors (e.g., plasmids) comprising a sequence encoding the inventive peptide, as well as host cells comprising such vectors. Methods for solid state protein synthesis and recombinant protein synthesis are well-known in the art. For example, "Molecular Cloning, A Laboratory Manual" (Sambrook et al., 3d Edition, Cold Spring Harbor Press), is a well-known reference detailing many suitable techniques for recombinant production of polypeptides. Accordingly, the invention provides the inventive peptide in recombinant form.

However it is made, the inventive peptide can be isolated and/or purified (or substantially isolated and/or substantially purified). Accordingly, the invention provides the inventive peptide in substantially isolated form (i.e., substantially isolated from other polypeptides or impurities). The peptide can be isolated from other peptides as a result of solid phase protein synthesis, for example. Alternatively, the peptide can be substantially isolated from other proteins after cell lysis from recombinant production. Standard methods of protein purification (e.g., HPLC) can be employed to substantially purify the inventive peptides. Thus, a preparation of the inventive polypeptide preferably is at least 90% free of other polypeptides and/or contaminants, and more preferably is at least about 95% free of other polypeptides and/or contaminants (such as at least about 97% or 98% free of other polypeptides and/or contaminants). In a most preferred embodiment, the invention provides a preparation of the inventive polypeptide that is greater than 99% free of other polypeptides and/or contaminants (e.g., greater than 99.5% or even 99.9% or even 99.99% free of other polypeptides).

In another embodiment, the invention provides a preparation of the inventive peptide in a number of formulations, depending on the desired use. For example, where the peptide is substantially isolated (or even nearly completely isolated from other proteins), it can be formulated in a suitable medium solution for storage (e.g., under refrigerated conditions or under frozen conditions). Such preparations can contain protective agents, such as buffers, preservatives, cryprotectants (e.g., sugars such as trehalose), etc. The form of such preparations can be solutions, gels, etc., and the inventive peptide can, in some embodiments, be prepared in lyophilized form. Moreover, such preparations can include other desired agents, such as small molecules or even other peptides and proteins, if desired. Indeed, the invention provides such a preparation comprising a mixture of different embodiments of the inventive peptide (e.g., a plurality of peptide species as described herein). Technology for preparing such compositions (e.g., lyophilization, preparation of protein solutions, etc.), is within the state of the art.

In another embodiment, the invention provides a composition comprising, consisting of, or consisting essentially of one or more of the inventive peptides (including mixtures thereof) and a physiologically acceptable carrier or a pharmaceutically acceptable carrier. Any carrier which can supply the peptide without destroying the vector within the carrier is a suitable carrier, and such carriers are well known in the art. The composition can be introduced to a patient using any suitable method which allows the patient to develop a CTL response. Such methods are well known in the art and include, for example, parenteral, oral, and topical administration. For example, a parenteral formulation could consist of a prompt or sustained release liquid preparation, dry powder, emulsion, suspension, or any other standard formulation. An oral formulation of the pharmaceutical composition could be, for example, a liquid solution, such as an effective amount of the composition dissolved in diluents (e.g., water, saline, juice, etc.), suspensions in an appropriate liquid, or suitable emulsions. An oral formulation could also be delivered in tablet form, and could include excipients, colorants, diluents, buffering agents, moistening agents, preservatives, flavoring agents, and pharmacologically compatible excipients. A topical formulation could include compounds to enhance absorption or penetration of the active ingredient through the skin or other affected areas, such as dimethylsulfoxide and related analogs. The physiological or pharmaceutical composition could also be delivered topically using a transdermal device, such as a patch, which could include the composition in a suitable solvent system with an adhesive system, such as an acrylic emulsion, and a polyester patch.

In addition to the inventive peptide carrier, as discussed above, the inventive composition can further comprise, consist of, or consist essentially of a T-helper epitope. Any suitable T-helper epitope which stimulates an immune response, such as for example the stimulation of CD4+ helper T cells and/or CD8+ CTLs, can be used. In a preferred embodiment, the T-helper epitope can be or comprise a peptide comprising, consisting of, or consisting essentially of a sequence of amino acids comprising, consisting of, or consisting essentially of TPPAYRPPNAPIL (SEQ ID NO:5).

In another embodiment, the invention provides a use of the inventive peptide or composition as a prophylactic or therapeutic vaccine for glioma. The inventive peptide can be used to treat any type of glioma, such as ependymomas, astrocytomas, oligodendrogliomas, glioblastomas, or mixed gliomas, or prophylactically in the prevention of such diseases. Thus, the invention includes the use of the inventive peptide and/or composition for preparation of a medicament useful for vaccinating a patient against glioma.

The invention further provides a method of vaccinating a patient against glioma, comprising, consisting of, or consisting essentially of introducing into the patient the inventive peptide or composition under conditions sufficient for said patient to develop a CTL response. As noted above, the composition can include a T-helper epitope, and inclusion of such epitope in the composition for use in the inventive method is preferred, but not necessary.

In another embodiment, the invention provides a use of a peptide having (e.g., comprising, consisting essentially of, or consisting of) the amino acid sequence TLADFDPRV (SEQ ID NO:6) as a prophylactic or therapeutic vaccine for glioma. The invention also provides a use of a composition comprising, consisting of, or consisting essentially of a peptide having the amino acid sequence TLADFDPRV (SEQ ID NO:6) and a physiologically acceptable carrier such as a prophylactic or therapeutic vaccine. Thus, the invention provides the use of such peptide for preparation of a medicament useful for vaccinating a patient against glioma.

This aspect of the invention further provides a method of vaccinating a patient against glioma, comprising, consisting of, or consisting essentially of introducing into the patient a peptide having (e.g., comprising, consisting essentially of, or consisting of) the amino acid sequence TLADFDPRV (SEQ ID NO:6) under conditions sufficient for said patient to develop a CTL response. In another embodiment, the invention provides a method of vaccinating a patient against glioma, comprising, consisting of, or consisting essentially of introducing into the patient a composition comprising, consisting of, or consisting essentially of a peptide having the sequence TLADFDPRV (SEQ ID NO:6) and a physiologically acceptable carrier. The physiological carrier can be a pharmaceutically acceptable carrier. As discussed above, any carrier which can supply the peptide without destroying the vector within the carrier is a suitable carrier, and such carriers are well known in the art. The composition can include a T-helper epitope, as noted above, and inclusion of such epitope in the composition for use in the inventive method is preferred, but not necessary. The peptide can be used to treat any type of glioma, such as ependymomas, astrocytomas, oligodendrogliomas, glioblastomas, or mixed gliomas, or prophylactically in the prevention of such diseases.

In accordance with the inventive method, regardless of the exact peptide used or the formulation of the composition, the patient can be any individual that has been diagnosed with glioma or is identified as at risk for developing glioma. In a preferred embodiment, the patient is a mammal. Even more preferably, the patient is human.

In accordance with the inventive method, the peptide or composition can be introduced to the patient by any suitable method, such as those described above. For therapeutic use, the peptide preferably is introduced locally into the situs of the glioma or systemically in amounts sufficient to treat the glioma. For prophylactic use, the peptide or composition is introduced into a patient in any suitable manner to deliver a sufficient amount of the protein to the patient to achieve a protective effect.

For therapeutic use, following introduction of the peptide or composition into the patient, in accordance with the inventive method, the patient's condition is monitored to assess the severity of the glioma. Suitable application of the inventive method will result in slowing of the progression of the glioma and, in preferred embodiments, result in plateauing of the progress of the disease. Indeed, in more preferred embodiments, application of the inventive method will result in shrinkage of glioma in the patient or even in substantial or complete remission of the glioma. Thus, while the inventive method can lead to a cure of the glioma in some patients, any degree of improvement in the prognosis of the patient following application of the inventive method is considered to be successful application. Moreover, it is to be understood that the inventive method can be used as monotherapy or adjunctively in combination with other therapeutic agents (e.g., chemotherapy or radiotherapy) or therapeutic methods.

For prophylaxis, following introduction of the inventive polypeptide or composition into the patient, the patient is suitably monitored to assess the development of glioma and/or continued risk of developing glioma. Successful prophylaxis can be measured by the absence of glioma in the patient for longer than the initial assessment of risk had predicted.

EXAMPLES

The following examples further illustrate the invention but, of course, should not be construed as in any way limiting its scope. Briefly, the examples demonstrate the generation of a potent agonist analogue peptide identified here, which can induce IL-13Rα2-specific CTL responses even more efficiently than the original IL-13Rα2$_{345-353}$. Three IL-13Rα2$_{345-353}$ analogue peptides have been created by substituting the carboxy-terminal isoleucine (I) for valine (V) and the amino terminal tryptophan (W) for either alanine (A), glutamic acid (E), or non-substituted (W) (designated as A1V9, E1V9 and V9, respectively). Relative immunogenicity of these IL-13Ralpha2 (345-353) peptide analogues was examined by stimulating peripheral blood cells (PBL) from glioma patients with dendritic cells (DC) loaded with each of these peptides. Among the peptide analogues tested, V9 was capable of inducing IL-13Rα2$_{345-353}$ specific CTL from PBL of glioma patients more efficiently than IL-13Rα2$_{345-353}$ consistently in all donors. These findings suggest that a highly antigenic IL-13Rα2 peptide-analogue V9 will be useful for the development of vaccines capable of expanding IL-13Rα2 specific CTL in glioma patients. The following examples also demonstrate the ability of the peptide EphA2$_{883-891}$ to induce an EphA2 specific CTL response, thus suggesting that the peptide would be useful in the development of additional vaccines for glioma.

Example 1

This example demonstrates the identification of modified peptides for IL-13Rα2$_{345-353}$ that enhance induction of the CTL response against native IL-13Rα2$_{345-353}$.

Three modified peptides were synthesized as listed in Table 1. The binding capability of these modified peptides was assessed using an HLA-A2 transfected T2 cell line. Aliquots of T2 cells were incubated with modified peptides or IL-13Rα2$_{345-353}$ at 1 nM overnight, and then examined for the surface expression levels of HLA-A2 on T2 cells by flow cytometry. Since stable binding of HLA-A2 with peptide epitopes further stabilizes the surface expression of HLA-A2 (Francini et al., 2002; Alves et al., 2003), quantitative expression levels of HLA-A2, which is indicated by Mean Fluorescence Intensity (MFI) in Table 1, correlate with the binding affinity of the peptide-epitopes that are co-incubated with the T2 cells. The modified peptides V9 and A1V9 possess higher binging affinity to HLA-A2 than the native IL-13Rα2$_{345-353}$ (Table 1), suggesting the possibility that these modified peptides are more immunogenic than the IL-13Rα2$_{345-353}$.

strated higher CTL activities than the native IL-13Rα2$_{345-353}$ in all four donors tested (data not shown).

Figure 2:
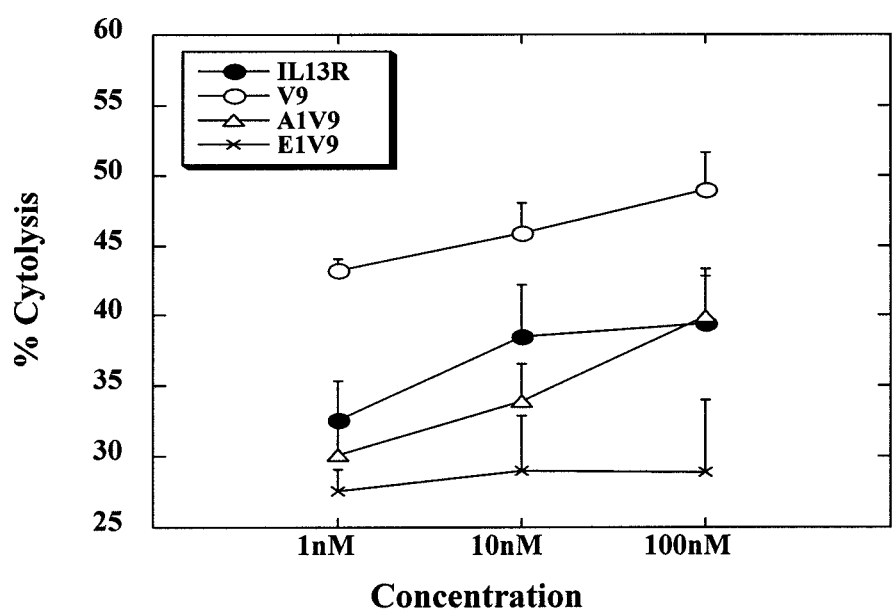
FIG. 2 graphically presents data demonstrating that the CTL line induced by the V9 peptide had increased lytic activity against T2 cells loaded with various concentrations of the wild type IL-13Rα2$_{345\text{-}353}$ peptide. The CTL lines induced by each of the 3 agonist analogues or the wild type peptide were examined for CTL activities against lower concentrations of target IL-13Rα2$_{345\text{-}353}$ peptide with T2 cells loaded with various concentrations (1-100 nM) of IL-13Rα2$_{345\text{-}353}$ by 4-Hr $^{51}$Cr-release assay (E/T ratio=50).

Subsequently, the sensitivity of the CTL lines induced by agonist analogues or the wild type peptide was examined with T2 cells loaded with various concentrations (1-100 nM) of the IL-13Rα2$_{345-353}$ peptide by 4-Hr $^{51}$Cr-release assay (FIG. 2). All CTL lines demonstrated peptide-dose dependent lytic activities against peptide-loaded T2 cells. The CTL line induced by the agonist analogue V9 demonstrated higher CTL activities than the wild type IL-13Rα2$_{345-353}$ at all peptide-concentrations examined (P=0.029, 0.039 and 0.018 at 1, 10 and 100 nM, respectively). It is noteworthy that the average percent lysis value achieved by V9-induced CTL with 1 nM IL-13Rα2$_{345-353}$ was higher than that demonstrated with wild type peptide-induced CTL with 100 nM peptide, although this did not demonstrate a statistical significance due to a large standard variation. These results indicate that the V9 peptide is more efficient than the wild type peptide in inducing CTL that are capable of recognizing low concentrations of the target wild type IL-13Rα2$_{345-353}$ peptide. This ability is important because human tumor cells

| Peptide | Amino Acid Sequence | Binding Index(MFI*) | Designation |
|---|---|---|---|
| WLPFGFILI (SEQ ID NO: 1) | native IL-13Rα2$_{345-353}$ | 237.4 | native |
| WLPFGFILV (SEQ ID NO: 2) | V9: I was replaced with V at P9 | 375.6 | V9 |
| ALPFGFILV (SEQ ID NO: 3) | A1V9: W→A at P1, and I→V at P9 | 462.8 | A1V9 |
| ELPFGFILV (SEQ ID NO: 4) | E1V9: W→E at P1, and I→V at P9 | 241.6 | E1V9 |
| (Control: Non peptide) | | 121.8 | |

*Mean Fluorescence Intensity at the peptide concentration of 1 nM

Example 2

This example demonstrates that CTL induced by the agonist analogue V9 recognized peptide IL-13Rα2$_{345-353}$ presented on HLA-A*0201 more efficiently than CTL induced by the wild type peptide.

Dendritic cells (DCs) derived from HLA-A*0201$^+$ glioma patients were pulsed with either V9, A1V9, E1V9, a control influenza (flu), or the wild type peptide (10 μg/ml), and used to stimulate autologous CD8$^+$ T cells. On day 7, the individual responder cell cultures were then restimulated once with autologous DCs loaded with the corresponding peptide used in the primary stimulation. Specific CTL activity of the induced T cell lines was first tested with T2 cells loaded with the wild type IL-13Rα2$_{345-353}$, or no peptide on day 10.

As depicted in FIG. 1, the T cells that had been stimulated with either wild type (IL-13R) or agonist analogues (V9, A1V9 and E1V9) efficiently lysed T2 target cells pulsed with 100 ng/ml wild type IL-13Rα2$_{345-353}$; whereas only low background lysis was observed in the absence of the peptide on T2 cells. T cells that had been stimulated with the control flu-peptide or no-peptide (control) did not demonstrate any lytic activity over background levels. These results demonstrated that the CTL lines induced with the wild type or agonist analogues recognized and lysed the cells presenting wild type IL-13Rα2$_{345-353}$ epitope specifically. In particular, the V9 peptide induced a significantly higher level of antigen-specific CTL response in comparison to the wild type IL-13Rα2$_{345-353}$ at each effector/target (E/T) ratio (p=0.018, 0.020 and 0.011 at an E/T ratio of 50, 25 and 12.5, respectively). The same set of experiments were repeated with at least three individual HLA-A2+ glioma patients, and the V9 peptide consistently demonexpress low levels of target CTL epitopes on their HLA-molecules (Bakker et al., 1995; Lupetti et al., 1998).

Example 3

This example demonstrates that CTL induced by modified peptides lysed HLA-A2+ glioma cells that express IL-13Rα2 more efficiently than CTL induced by the native peptide.

The ability of modified peptides, such as IL-13Rα2-V9, to enhance the CTL activity against HLA-A2+ human glioma cells that endogenously expressed and presented IL-13Rα2-derived epitopes was examined. Human glioma cell lines U251 and SNB19 express HLA-A2 and IL-13Rα2, whereas human glioma cell line A172 expresses IL-13Rα2 but not HLA-A2 (Okano et al., 2002). Therefore, U251 and SNB19 were used as relevant target glioma cells, while A172 served as a negative control line to demonstrate HLA-A2-restriction of the response.

Figure 3:
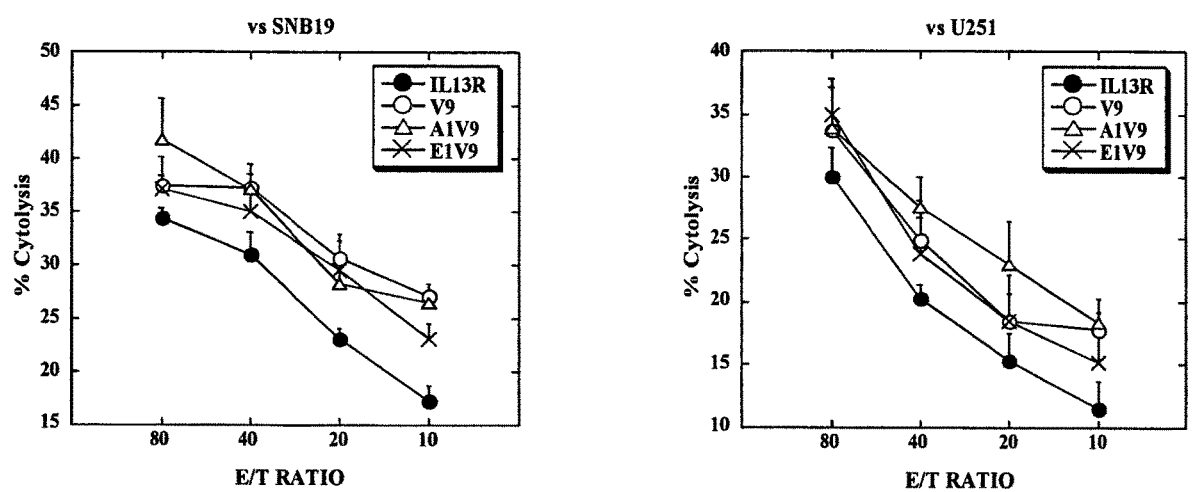
FIG. 3 graphically presents data demonstrating that the modified peptides induced a higher magnitude of CTL reactivity than the native IL-13Rα2$_{345\text{-}353}$ against human glioma cell lines. CD8+ cells derived from an HLA-A2+ glioma patient were stimulated with native IL-13Rα2$_{345\text{-}353}$ (●), IL-13Rα2-V9 (○), IL-13Rα2-A1V9 (Δ), or IL-13Rα2-E1V9 (X). On day 10, the cells were tested for lytic ability against human glioma cells SNB19 and U-251 (both are IL-13Rα+/HLA-A2+) using 4-Hr $^{51}$Cr-release assay. Against SNB19 glioma cells, $p<0.05$ at all E/T ratios for IL-13Rα2-V9 vs. native IL-13Rα2$_{345\text{-}353}$ as well as IL-13Rα2-A1V9 vs. native IL-13Rα2$_{345\text{-}353}$ by two-tailed Student-t tests. Against U251 glioma cells, $p<0.05$ at E/T ratio of 10 and 40 for IL-13Rα2-V9 vs. native IL-13Rα2$_{345\text{-}353}$ as well as IL-13Rα2-A1V9 vs. native IL-13Rα2$_{345\text{-}353}$ by two-tailed Student-t tests. IL-13Rα2-E1V9 did not improve the CTL reactivity for a statistically significant level in comparison to the native. The data presented represent one of three experiments with different donors with similar results.

The lytic ability of the peptide-induced CTL lines against these glioma cells was examined using 4-hr $^{51}$Cr-release assays. As illustrated in FIG. 3, the U-251 and SNB19 cell lines were highly susceptible to cytotoxic activity of all CTL cell lines that had been induced with IL-13Rα2$_{345-353}$ or each of its modified peptides. A172 cells, in contrast, were not lysed beyond the background level (<10%) by any of the CTL lines tested, suggesting that the IL-13Rα2$_{345-353}$ or modified peptide-induced CTL lines lysed SNB19 and U-251 glioma cells in an HLA-A2 restricted manner (data not shown). The T cells stimulated with a melanoma associated antigen epitope Mart-1 (27-35) and T cells with no peptide stimulation showed only background level (<10%) lysis at all Effector/Target (E/T) ratios tested (data not shown). In this particular patient, both IL-13Rα2-V9 and -A1V9 induced higher levels of lysis of SNB19 and U-251 in each E/T ratio in comparison to the native IL-13Rα2$_{345-353}$ peptide.

Figure 4:
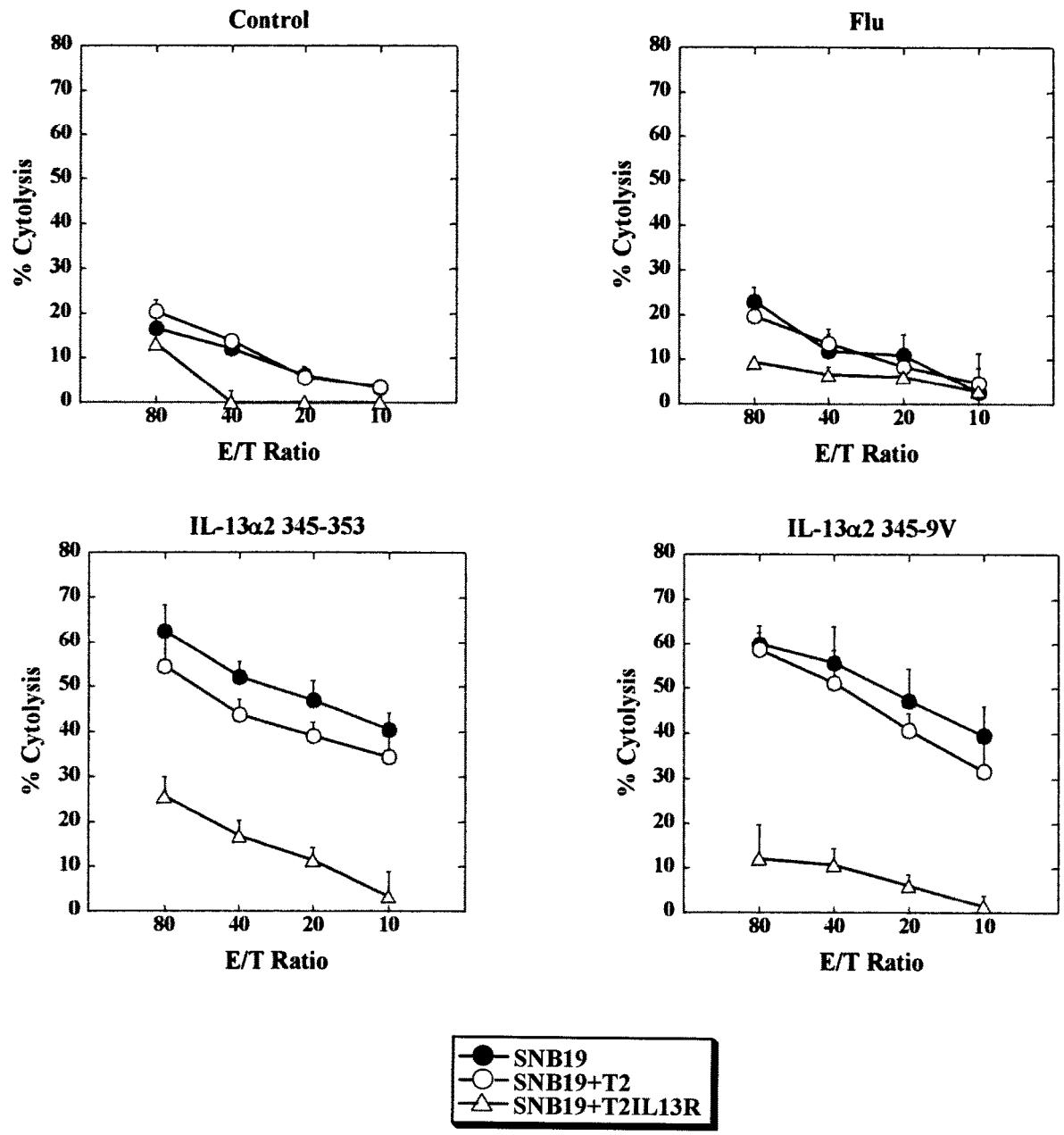
FIG. 4 graphically presents data demonstrating that the addition of "cold" T2 cells pulsed with IL-13Rα2$_{345\text{-}353}$ inhibited the CTL activities indicating the antigen-specificity of the CTL lines. The CTL lines induced with each peptide were incubated for 4 h with $^{51}$Cr-labeled human glioma cell lines SNB19 at the indicated E:T ratios for evaluation of specific lytic ability (●). For the cold target inhibition assay, $^{51}$Cr-labeled target SNB19 cells (1×10$^3$ cells/well) and cold T2 cells (1×10$^4$ cells/well) pulsed with (Δ) or without (○) peptide IL-13Rα2$_{345\text{-}353}$ were incubated with the CTLs.

To determine the specificity of the lytic activity, cold target competition experiments were performed by addition of non-radiolabeled (cold) T2 cells pulsed with IL-13Rα2$_{345-353}$ peptide in the 4-h $^{51}$Cr-release assay (FIG. 4). The anti-SNB19 glioma cell lytic activities by the CTL lines induced by the native IL-13Rα2$_{345-353}$ or IL-13Rα2-V9 were almost completely inhibited by the addition of the cold T2 cells pulsed IL-13Rα2$_{345-353}$. The CTL activities, however, were not inhibited by the addition of non-peptide pulsed cold T2 cells, demonstrating that the lytic ability of the CTLs was specific for the epitope IL-13Rα2$_{345-353}$.

Figure 5:
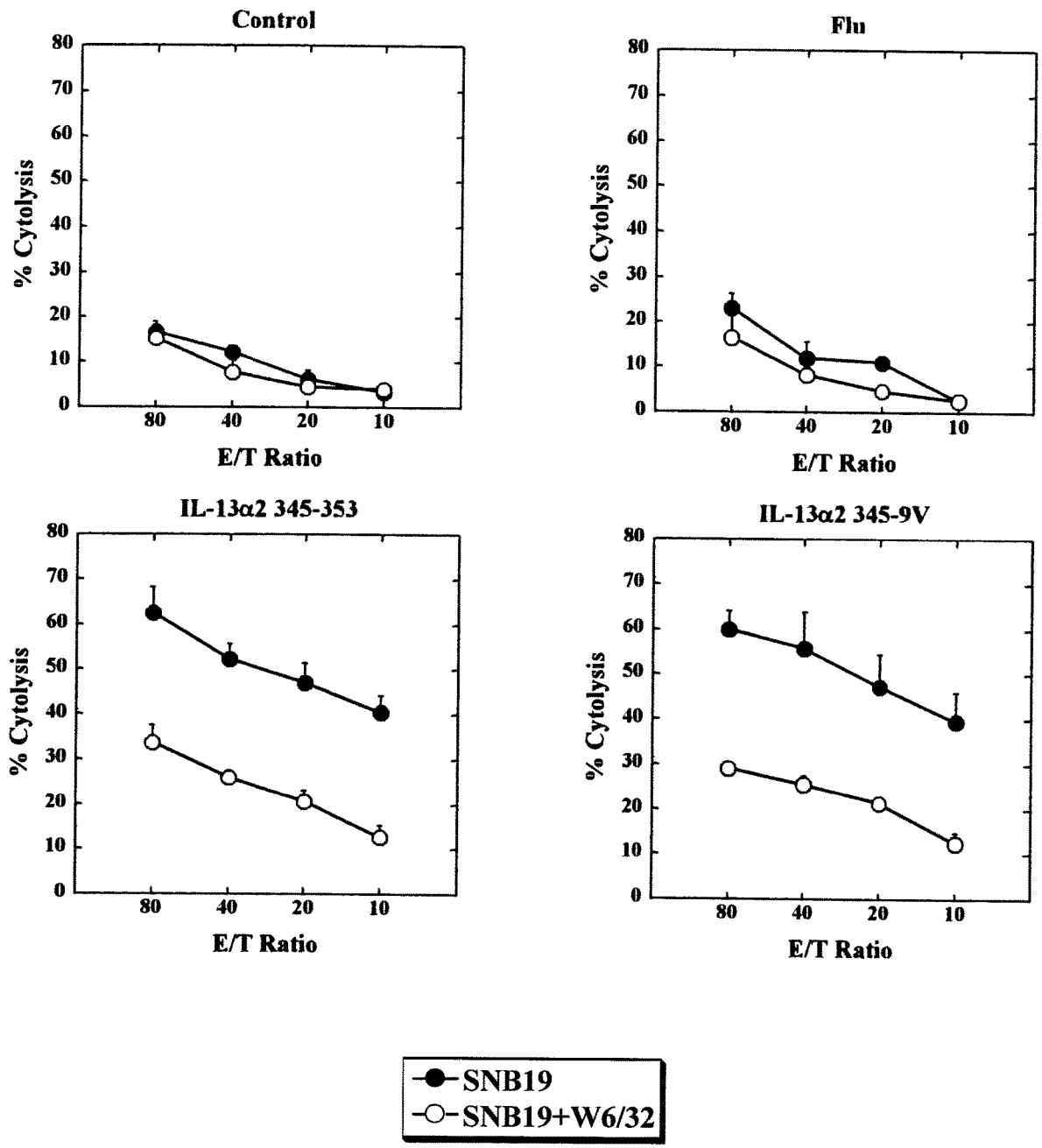
FIG. 5 graphically presents data demonstrating that the addition of anti-HLA-A2 antibody inhibited the CTL activities indicating HLA-A2-restricted recognition of the CTL lines. The CTL lines induced with each peptide were incubated for 4 h with $^{51}$Cr-labeled human glioma cell line SNB19 at the indicated E:T ratios for evaluation of specific lytic ability (●). Anti-HLA-A2 antibody (W6/32; 10 µg/ml) was added to block the function of HLA-A2 mediated recognition by the T cells (○).

Furthermore, anti-HLA-A2 antibody (W6/32) was used to block the HLA-A2 mediated signaling in the CTL reactivity. As illustrated in FIG. 5, addition of this antibody inhibited the CTL-mediated lysis, confirming that the anti-glioma CTL reactivity induced by these peptides was HLA-A2 restricted.

Example 4

This example demonstrates the vaccination of HLA-A2 transgenic (HHD) mice with IL-13Rα2-derived CTL epitopes.

In order to examine whether immunization with IL-13Rα2$_{345-353}$ and/or its modified peptides can elicit CTL responses in vivo, and also to examine whether induced CTL responses can mediate therapeutic anti-tumor responses against IL-13Rα2$_{345-353}$-expressing brain tumors, the HHD mice were obtained from Dr. Francois A. Lemonnier (Pasteur Institute, Paris). HHD mice are $D^b \times \beta 2$ microglobulin (β2M) null, and transgenic for modified HLA-A2.1-β2 microglobulin single chain (HHD gene) (Pascolo et al., 1997). In vivo experiments showed that HHD mice exhibit HLA-A2-restricted responses to multiepitope proteins such as intact influenza virus (Pascolo et al., 1997) and novel cancer associated antigens, such as EphA2 (Alves et al., 2003), HER-2/neu and hTERT (Scardino et al., 2002), MAGE (Graff-Dubois et al., 2002) and a novel breast carcinoma associated BA46 (Carmon et al., 2002). Hence, these mice are a useful tool for the identification and characterization of potential tumor-derived, HLA-A2-restricted CTL epitopes.

To create an HHD mouse-syngeneic tumor cell line that expresses IL-13Rα2, HHD gene-transfected EL4 lymphoma cells (EL4-HHD) were obtained. EL4-HHD cells have been generated from EL4 by depletion of $D^b \times \beta 2M$ and insertion of modified HLA-A2.1-β2M single chain (Pascolo et al., 1997), thereby allowing syngeneic transplantation in HHD mice. EL4-HHD cells were stably transfected with an expression plasmid encoding IL-13Rα2. The cell line (EL4-HHD-IL-13Rα2) expressed IL-13Rα2 protein and formed tumors both in subcutaneous (s.c.) and intracranial (i.c.) space following injections to syngeneic HHD mice.

Example 5

This example demonstrates that in vivo immunization of HHD mice with the modified peptides induced higher magnitudes of CTL responses than the native peptide against the target cells expressing IL-13Rα2$_{345-353}$.

HHD mice received (on days 7 and 14) s.c. injections of 100 µg of peptide IL-13Rα2-V9, -A1V9, 13Rα2$_{345-353}$, or MART-1$_{27-35}$ emulsified in incomplete Freund's adjuvant (IFA) in the presence of 140 µg of the I-A$^b$-restricted HBVcore$_{128}$ (TPPAYRPPNAPIL) (SEQ ID NO:5) T-helper epitope, which stimulates a CD4+ helper T cell response, thereby promoting the stimulation of CD8+ CTLs. Control animals received IFA containing HBV helper-peptide only. Eleven days after the last immunization, the animals were sacrificed, and 5×10 spleen cells (SPCs) were stimulated in vitro with the same peptide that was used for in vivo stimulation (10 µM). On day 6 of culture, the bulk populations were tested for specific cytotoxicity against the EL4-HHD cells expressing IL-13Rα2 or EL4-HHD pulsed with IL-13Rα2$_{345-353}$.

EL4-HHD-13Rα2 and EL4-HHD were labeled with 100 µCi of $^{51}$Cr for 60 min, plated in 96-well V-bottomed plates (3×10$^3$ cell/well). Labeled EL4-HHD were pulsed with IL-13Rα2$_{345-353}$ (1 µM) at 37° C. for 2 h. Control target cells were pulsed with no peptides. Stimulated SPCs were then added as effector cells and incubated at 37° C. for 4 h. One hundred µl of supernatant were collected and radioactivity measured in a gamma counter.

Figure 6:
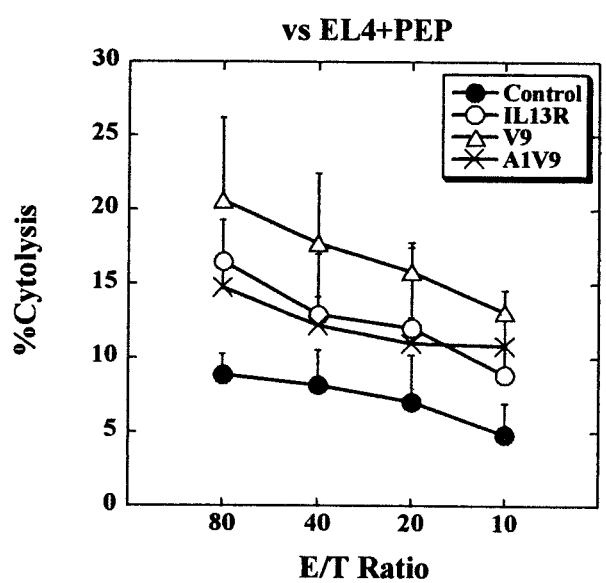
FIG. 6 graphically presents data demonstrating that the modified peptides induced higher magnitude of CTL reactivity than the native IL-13Rα2$_{345\text{-}353}$ against EL4-HHD loaded with the native IL-13Rα2$_{345\text{-}353}$ SPCs obtained from HHD mice that had been immunized with either control MART-1$_{27\text{-}35}$ (●), native IL-13Rα2$_{345\text{-}353}$ (○), IL-13Rα2-V9 (Δ) or IL-13Rα2-A1V9 (X) were tested for their specific lytic activity against EL4-HHD cells pulsed with the native IL-13Rα2$_{345\text{-}353}$ by standard 4 hr-$^{51}$Cr-release assays.

FIG. 6 demonstrates that the CTL responses induced by the modified peptides were able to lyse T2 cells loaded with the native IL-13Rα2$_{345-353}$. Control non-pulsed EL4-HHD cells were not lysed by the CTLs beyond background levels (shown in FIG. 7). Furthermore, the immunization with IL-13Rα2-V9 displayed a trend toward higher levels of CTL reactivity against the EL4-HHD cells pulsed with the native IL-13Rα2$_{345-353}$ peptide than other peptides examined, although the difference was not statistically significant due to the variation within the triplicated samples. These data support the previous set of data with human HLA-A2+ patient derived T cells, in which the modified peptides induced higher levels of anti-IL-13Rα2$_{345-353}$ CTL response than the native peptide.

Figure 7:
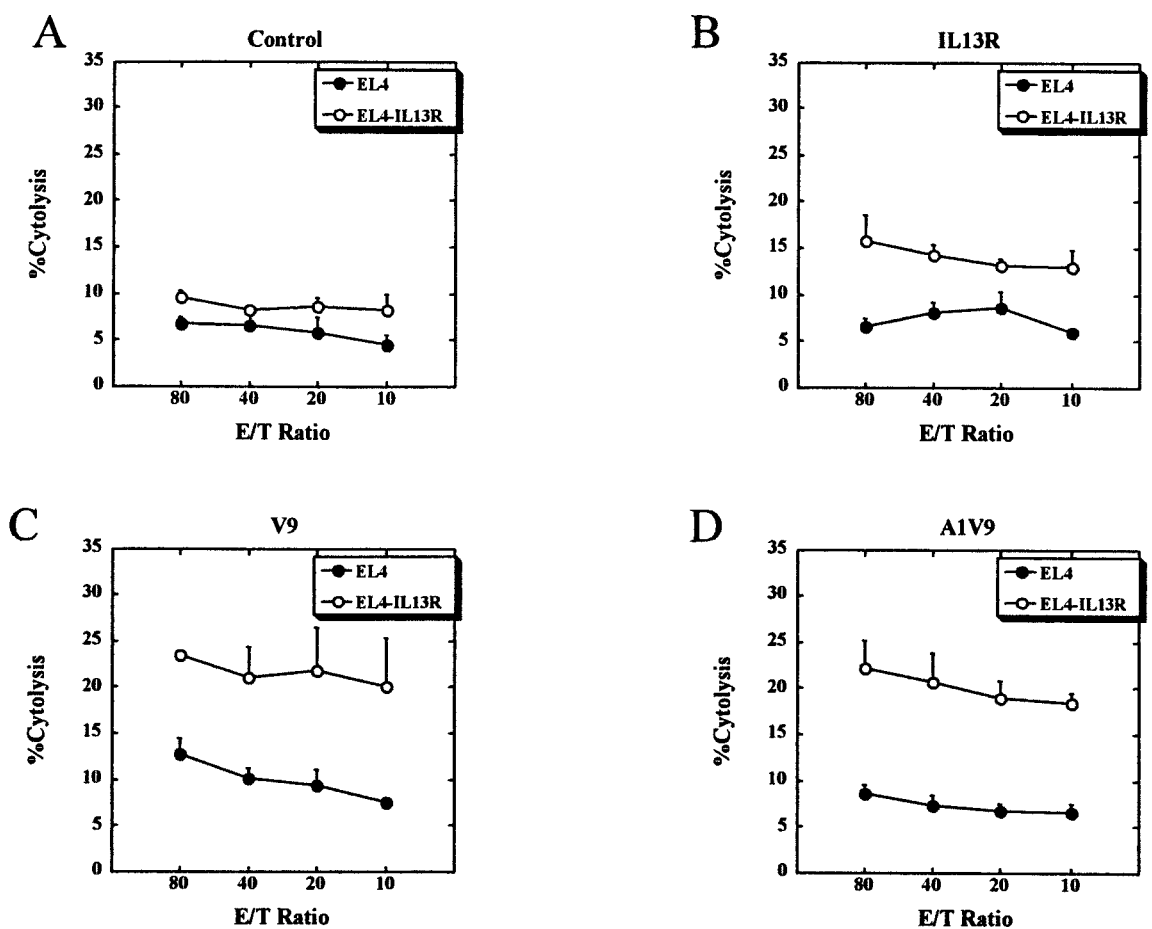
FIG. 7 graphically presents data demonstrating that the modified peptides induced a higher magnitude of CTL reactivity than the native IL-13Rα2$_{345\text{-}353}$ against EL4-HHD-IL-13Rα2. SPCs obtained from HHD mice that had been immunized with either control MART-1$_{27\text{-}35}$ (A), native IL-13Rα2$_{345\text{-}353}$ (B), IL-13Rα2-V9 (C), or IL-13Rα2-A1V9 (D) were tested their specific lytic activity against EL4-HHD-IL-13Rα2 (○) or control EL4-HHD (●) by standard 4 hr-$^{51}$Cr-release assays.

The ability of the same HHD mice-derived CTLs used in FIG. 6 to lyse EL4-HHD-IL-13Rα2 cells was examined in order to evaluate the ability of the CTLs to recognize the IL-13Rα2$_{345-353}$ peptide that is naturally processed by cells that endogenously express IL-13Rα2. FIG. 7 illustrates that immunization with the IL-13Rα2$_{345-353}$, IL-13Rα2-V9 or -A1V9 induced a specific CTL activity against EL4-HHD-IL-13Rα2 cells. The CTL activities were antigen-specific because control EL4-HHD were not lysed beyond the background level. Modified peptides IL-13Rα2-V9 and -A1V9 induced higher magnitude of CTL activities in comparison to native IL-13Rα2$_{345-353}$ against the EL4-HHD-IL-13Rα cells (p<0.05 at all effector/target ratios). The in vivo anti-tumor effect of vaccinations with the IL-13Rα2$_{345-353}$ or modified IL-13Rα2 peptides in HHD mice bearing EL4-HHD-IL-13Rα2 tumors is currently being evaluated.

Example 6

This example demonstrates that EphA2 has available HLA-A2-restricted CTL epitopes.

Figure 8:
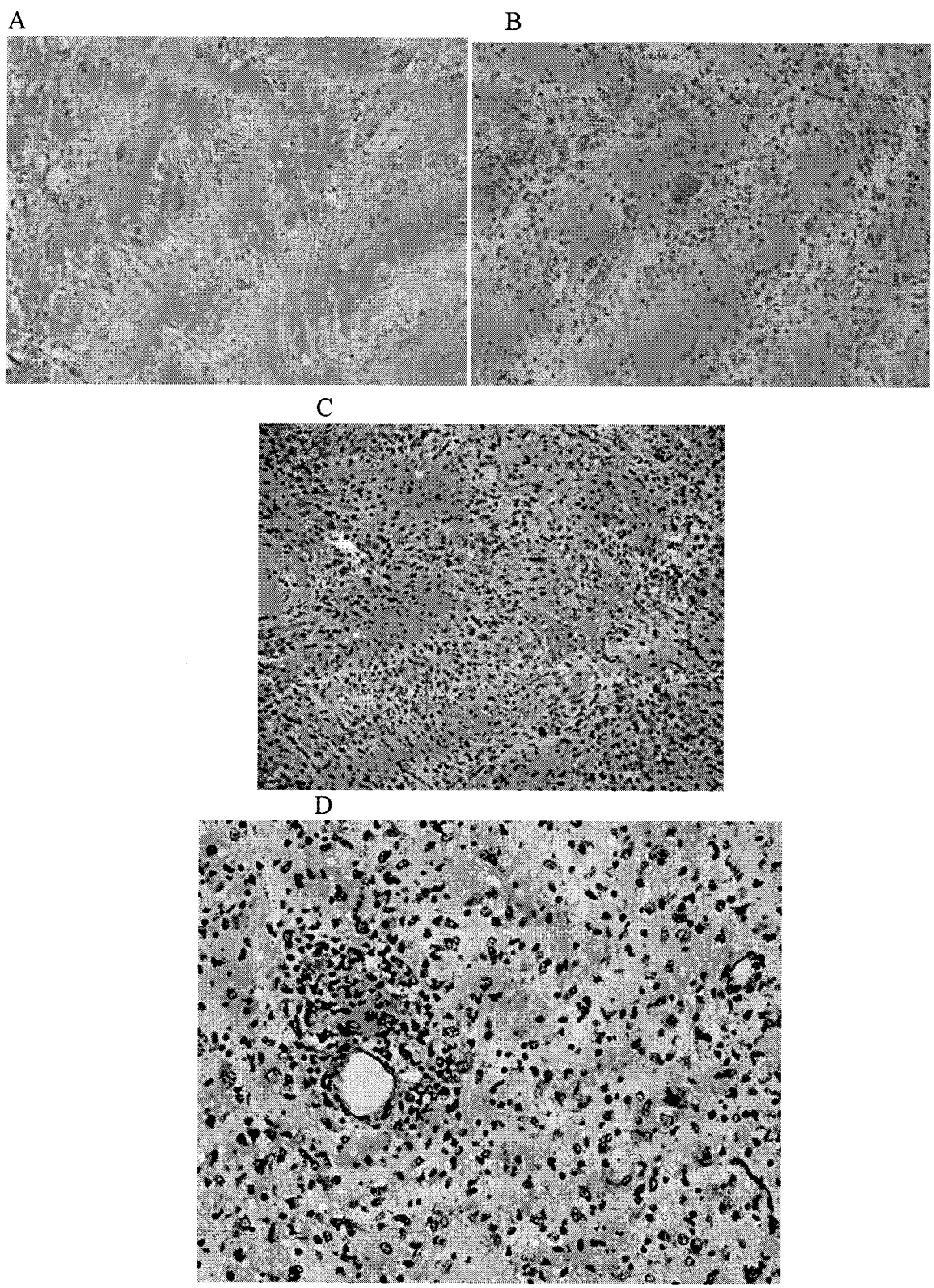
FIG. 8 depicts the expression of EphA2 protein in glioblastoma multiforme (GBM) and anaplastic astrocytoma (AA). Paraffin embedded sections of surgical specimens obtained from patients with GBM (A-C) or AA (D) were deparaffinized and stained with anti-EphA2 polyclonal antibody (C-20: Santa Cruz Biotechnology, Inc., Santa Cruz, Calif.), or control rabbit IgG (upper right corner window for each sample). Relatively dense staining on endothelia and tumor cells surrounding the vessel was observed (D). Nine of fourteen GBM and six of nine AA cases examined were positive for EphA2 (not shown). Original magnification; ×20.
Figure 9:
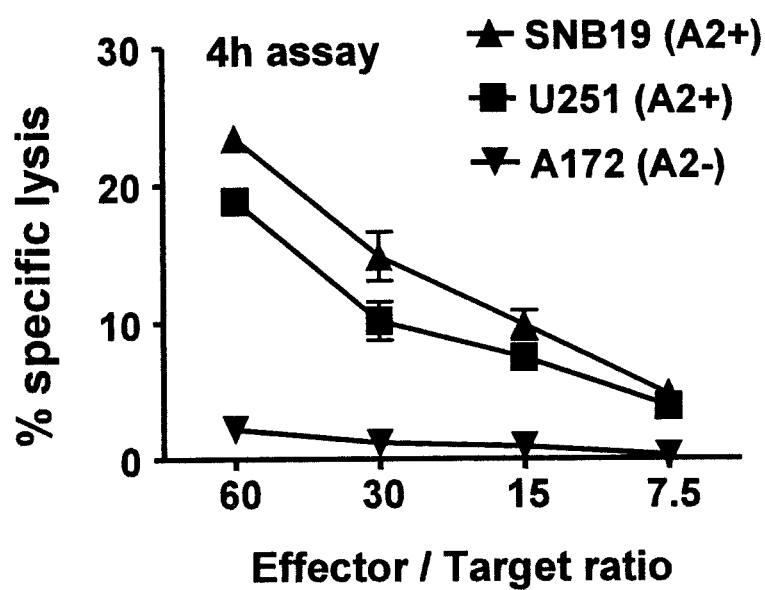
FIG. 9 graphically presents data demonstrating that the CD8+ cells stimulated with EphA2$_{883\text{-}891}$ elicited CTL responses against human glioma cells expressing HLA-A2 and EphA2 protein. CD8+ T cells from an HLA-A2+ glioma patients were stimulated with DCs loaded with EphA2$_{883\text{-}891}$ for 10 days. These T cells were then tested for their lytic activity against human glioma cells SNB19

EphA2 is an attractive tumor-associated antigen and a target for tumor-vaccines, as 5 HLA-A2 and 3 DR4 T cell epitopes have been previously identified (Tatsumi et al., 2003). As shown in FIG. 8, 9 of 14 human glioblastoma multiforme (GBM) and 6 of 9 anaplastic astrocytoma (AA) cases express high levels of EphA2. In addition, anti-glioma CTL reactivity has been induced in CD8+ cells obtained from HLA-A2+ glioma patients by stimulation with the EphA2$_{883-891}$ epitope (FIG. 9). This response was specific for the EphA2$_{883-891}$ epitope because the parallel assay using T2 cells loaded with EphA2$_{883-891}$ demonstrated a peptide-specific response in comparison to the control unloaded T2 target (not shown). These data strongly suggest that EphA2$_{883-891}$ can serve as a CTL epitope.

BIBLIOGRAPHY i. Alves, P. M., Faure, O., Graff-Dubois, S., Gross, D. A., Cornet, S., Chouaib, S., Miconnet, I., Lemonnier, F. A., and Kosmatopoulos, K. (2003). EphA2 as target of anticancer immunotherapy: identification of HLA-A*0201-restricted epitopes. Cancer Res 63, 8476-8480.

ii. Bakker A B., Marland G., de Boer A J., Huijbens R J., Danen E H., Adema G J., and Figdor C G. (1995). Generation of antimelanoma cytotoxic T lymphocytes from healthy donors after presentation of melanoma-associated antigen-derived epitopes by dendritic cells in vitro. Cancer Res. 55, 5330-5334.

iii. Bigner D D, Pitts O M, and Wikstrand C J (1981). Induction of lethal experimental allergic encephalomyelitis in non-human primates and guinea pigs with human glioblastoma multiforme tissue. J Neurosurg 55, 32-42.

iv. Bownds, S., Tong-On, P., Rosenberg, S. A., and Parkhurst, M. (2001). Induction of tumor-reactive cytotoxic T-lymphocytes using a peptide from NY-ESO-1 modified at the carboxy-terminus to enhance HLA-A2.1 binding affinity and stability in solution. J Immunother. 24, 1-9.

v. Brantley D M, Cheng N, Thompson E J, Lin Q, Brekken R A, Thorpe P E, Muraoka R S, Cerretti D P, Pozzi A, Jackson D, et al. (2002). Soluble Eph A receptors inhibit tumor angiogenesis and progression in vivo. Oncogene 21, 7011-7026.

vi. Carmon, L., Bobilev-Priel, !., Brenner, B., Bobilev, D., Paz, A., Bar-Haim, E., Tirosh, B., Klein, T., Fridkin, M., Lemonnier, F., Tzehoval, E., and Eisenbach, L. (2002). Characterization of novel breast carcinoma-associated BA46-derived peptides in HLA-A2.1/D(b)-beta2m transgenic mice. J. Clin. Invest 110, 453-462.

vii. Chen, J L, Dunbar, P. R., Gileadi, U., Jager, E., Gnjatic, S., Nagata, Y., Stockert, E., Panicali, D. L., Chen, Y. T., Knuth, A., Old, L. J., and Cerundolo, V. (2000). Identification of NY-ESO-1 peptide analogues capable of improved stimulation of tumor-reactive CTL. J Immunol 165, 948-955.

viii. Debinski, W. and Gibo, D. M. (2000). Molecular expression analysis of restrictive receptor for interleukin 13, a brain tumor-associated cancer/testis antigen. Mol. Med 6, 440-449.

ix. Debinski, W., Gibo, D. M., Slagle, B., Powers, S. K., and Gillespie, G. Y. (1999). Receptor for interleukin 13 is abundantly and specifically over-expressed in patients with glioblastoma multiforme. Int. J. Oncol. 75, 481-486.

x. Debinski, W., Slagle, B., Gibo, D. M., Powers, S. K., and Gillespie, G. Y. (2000). Expression of a restrictive receptor for interleukin 13 is associated with glial transformation. J. Neurooncol. 48, 103-111.

xi. Francini, G., Scardino, A., Kosmatopoulos, K., Lemonnier, F. A., Campoccia, G., Sabatino, M., Pozzessere, D., Petrioli, R., Lozzi, L., Neri, P., Fanetti, G., Cusi, M. G., and Correale, P. (2002). High-affinity HLA-A(*)02.01 peptides from parathyroid hormone-related protein generate in vitro and in vivo antitumor CTL response without autoimmune side effects. J. Immunol 169, 4840-4849.

xii. Graff-Dubois, S., Faure, O., Gross, D. A., Alves, P., Scardino, A., Chouaib, S., Lemonnier, F. A., and Kosmatopoulos, K. (2002). Generation of CTL recognizing an HLA-A*0201-restricted epitope shared by MAGE-A1, -A2, -A3, -A4, -A6, -A10, and -A12 tumor antigens: implication in a broad-spectrum tumor immunotherapy. J. Immunol 169, 575-580.

xiii. Greten, T. F., Korangy, F., Neumann, G., Wedemeyer, H., Schlote, K., Heller, A., Scheffer, S., Pardoll, D. M., Garbe, A. I., Schneck, J. P., and Manns, M. P. (2002). Peptide-beta2-microglobulin-MHC fusion molecules bind antigen-specific T cells and can be used for multivalent MHC-Ig complexes. J. Immunol. Methods 277, 125-135.

xiv. Gross D A, Graff-Dubois S, Opolon P, Cornet S, Alves P, Naceur-Griscelli O, Faure O, Guillaume P, Firat H, Chouaib S, et al. (2004). High vaccination efficiency of low-affinity epitopes in antitumor immunotherapy. J Clin Invest 113, 425-433.

xv. Hatano M, Kuwashima N, Tatsumi T, Dusak J E, Nishimura F, Reilly K M, Storkus W J, and Okada H (2004). Vaccination with EphA2-derived T cell-epitopes promotes immunity against both EphA2-expressing and EphA2-negative tumors. J Transl Med 2, 40.

xvi. Herrem C J, Tatsumi T, Olson K S, Shirai K, Finke J H, Bukowski R M, Zhou M, Richmond A L, Derweesh I, Kinch M S, et al. (2005). Expression of EphA2 is prognostic of disease-free interval and overall survival in surgically treated patients with renal cell carcinoma. Clin Cancer Res 11, 226-231.

xvii. Kinch M S and Carles-Kinch K (2003). Overexpression and functional alterations of the EphA2 tyrosine kinase in cancer. Clin Exp Metastasis 20, 59-68.

xviii. Lupetti, R., Pisarra, P., Verrecchia, A., Farina, C., Nicolini, G., Anichini, A., Bordignon, C., Sensi, M., Parmiani, G., and Traversari, C. (1998). Translation of a retained intron in tyrosinase-related protein (TRP) 2 mRNA generates a new cytotoxic T lymphocyte (CTL)-defined and shared human melanoma antigen not expressed in normal cells of the melanocytic lineage. J. Exp. Med. 188, 1005-1016.

xix. Ogawa K, Pasqualini R, Lindberg R A, Kain R, Freeman A L, and Pasquale E B (2000). The ephrin-A1 ligand and its receptor, EphA2, are expressed during tumor neovascularization. Oncogene 19, 6043-6052.

xx. Okada, H., Tahara, H., Shurin, M. R., Attanucci, J., Giezeman-Smits, K M., Fellows, K. W., Lotze, M. T., Chambers, W. H., and Bozik, M. E. (1998). Bone marrow derived dendritic cells pulsed with a tumor specific peptide elicit effective anti-tumor immunity against intracranial neoplasms. Int. J. Cancer 78, 196-201.

xxi. Okada, H., Villa, L. A., Attanucci, J., Erff, M., Fellows, W. K., Lotze, M. T., Pollack, I. F., and Chambers, W. H. (2001). Cytokine Gene Therapy of Gliomas: Effective Induction of Therapeutic Immunity to Intracranial Tumors by Peripheral Immunization with Interleukin-4 Transduced Glioma Cells. Gene Ther. 8, 1157-1166.

xxii. Okada H, Lieberman F S, Edington H D, Witham T F, Wargo M J, Cai Q, Elder E H, Whiteside T L, Schold S C Jr, and Pollack I F (2003). Autologous glioma cell vaccine admixed with interleukin-4 gene transfected fibroblasts in the treatment of recurrent glioblastoma: preliminary observations in a patient with a favorable response to therapy. J Neuro-Oncol 64, 13-20.

xxiii. Okada H, Pollack I F, Lieberman F, Lunsford L D, Kondziolka D, Schiff D, Attanucci J, Edington H, Chambers W, Kalinski P, et al. (2001). Gene therapy of malignant gliomas: a pilot study of vaccination with irradiated autologous glioma and dendritic cells admixed with IL-4 transduced fibroblasts to elicit an immune response. Hum Gene Ther 12, 575-595.

xxiv. Okano, F., Storkus, W. J., Chambers, W. H., Pollack, I. F., and Okada, H. (2002). Identification of a novel HLA-A*0201 restricted cytotoxic T lymphocyte epitope in a human glioma associated antigen, interleukin-13 receptor 2 chain. Clin. Cancer Res. 8, 2851-2855.

xxv. Pascolo S, Bervas N, Ure J M, Smith A G, Lemonnier F A, and Perarnau B (1997). HLA-A2.1-restricted education and cytolytic activity of CD8(+) T lymphocytes from beta2 microglobulin (beta2m) HLA-A2.1 monochain transgenic H-2Db beta2m double knockout mice. J Exp Med 185, 2043-2051.

xxvi. Riker A, Cormier J, Panelli M, Kammula U, Wang E, Abati A, Fetsch P, Lee K H, Steinberg S, Rosenberg S, et al. (1999). Immune selection after antigen-specific immunotherapy of melanoma. Surgery 126, 112-120.

xxvii. Scardino, A., Gross, D. A., Alves, P., Schultze, J. L., Graff-Dubois, S., Faure, O., Tourdot, S., Chouaib, S., Nadler, L. M., Lemonnier, F. A., Vonderheide, R. H., Cardoso, A. A., and Kosmatopoulos, K. (2002). HER-2/neu and hTERT cryptic epitopes as novel targets for broad spectrum tumor immunotherapy. J. Immunol 168, 5900-5906.

xxviii. Tatsumi T, Herrem C J, Olson W C, Finke J H, Bukowski R M, Kinch M S, Ranieri E, and Storkus W J (2003). Disease stage variation in CD4+ and CD8+ T-cell reactivity to the receptor tyrosine kinase EphA2 in patients with renal cell carcinoma. Cancer Res 63, 4481-4489.

xxix. Wen P Y and Kesari S (2004). Malignant gliomas. Curr Neurol Neurosci Rep 4, 218-227.

xxx. Yu J S, Liu G, Ying H, Yong W H, Black K L, and Wheeler C J (2004). Vaccination with tumor lysate-pulsed dendritic cells elicits antigen-specific, cytotoxic T-cells in patients with malignant glioma. Cancer Res 64, 4973-4979.

xxxi. Zelinski D P, Zantek N D, Stewart J C, Irizarry A R, and Kinch M S (2001). EphA2 overexpression causes tumorigenesis of mammary epithelial cells. Cancer Res 61, 2301-2306.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

SEQUENCE LISTING

```
<160> NUMBER OF SEQ ID NOS: 6

<210> SEQ ID NO 1
<211> LENGTH: 9
<212> TYPE: PRT
<213> ORGANISM: Artificial Sequence
<220> FEATURE:
<223> OTHER INFORMATION: Amino acid residues 345-353 of Interleukin-13
      Receptor alpha

<400> SEQUENCE: 1

Trp Leu Pro Phe Gly Phe Ile Leu Ile
1               5

<210> SEQ ID NO 2
<211> LENGTH: 9
<212> TYPE: PRT
<213> ORGANISM: Artificial Sequence
<220> FEATURE:
<223> OTHER INFORMATION: Amino acid residues 345-353 of Interleukin-13
      Receptor alpha 2 with mutation of I to V at position 353

<400> SEQUENCE: 2
```

```
Trp Leu Pro Phe Gly Phe Ile Leu Val
1               5

<210> SEQ ID NO 3
<211> LENGTH: 9
<212> TYPE: PRT
<213> ORGANISM: Artificial Sequence
<220> FEATURE:
<223> OTHER INFORMATION: Amino acid residues 345-353 of Interleukin-13
      Receptor alpha with mutation of W to A at position 345 and I to V
      at position 353

<400> SEQUENCE: 3

Ala Leu Pro Phe Gly Phe Ile Leu Val
1               5

<210> SEQ ID NO 4
<211> LENGTH: 9
<212> TYPE: PRT
<213> ORGANISM: Artificial Sequence
<220> FEATURE:
<223> OTHER INFORMATION: Amino acid residues 345-353 of Interleukin-13
      Receptor alpha with mutation of W to E at position 345 and I to V
      at position 353

<400> SEQUENCE: 4

Glu Leu Pro Phe Gly Phe Ile Leu Val
1               5

<210> SEQ ID NO 5
<211> LENGTH: 13
<212> TYPE: PRT
<213> ORGANISM: Artificial Sequence
<220> FEATURE:
<223> OTHER INFORMATION: Synthetic

<400> SEQUENCE: 5

Thr Pro Pro Ala Tyr Arg Pro Pro Asn Ala Pro Ile Leu
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Amino acid residues 883-891 of EphA2 (Tatsumi
      et al., Cancer Res., 63: 4481 - 4489 (2003)).

<400> SEQUENCE: 6

Thr Leu Ala Asp Phe Asp Pro Arg Val
1               5
```

The invention claimed is:

1. A composition comprising a peptide consisting of the amino acid sequence of ALPFGFILV (SEQ ID NO: 3), a peptide consisting of the amino acid sequence of TLADFDPRV (SEQ ID NO: 6), and a physiologically-acceptable carrier.

2. The composition of claim 1, wherein the carrier is a pharmaceutically-acceptable carrier.

3. The composition of claim 1, further comprising a T-helper epitope consisting of TPPAYRPPNAPIL (SEQ ID NO: 5).

4. The composition of claim 2, which is formulated for injection.

5. The composition of claim 4, which is formulated for parenteral injection.

6. The composition of claim 3, wherein the carrier is a pharmaceutically-acceptable carrier.

7. The composition of claim 6, which is formulated for injection.

8. The composition of claim 7, which is formulated for parenteral injection.

* * * * *